# (12) United States Patent
Yoshida

(10) Patent No.: US 10,808,013 B2
(45) Date of Patent: Oct. 20, 2020

(54) MUTANT IMMUNOGLOBULIN κ CHAIN VARIABLE REGION-BINDING PEPTIDE

(71) Applicant: Kaneka Corporation, Osaka (JP)

(72) Inventor: Shinichi Yoshida, Hyogo (JP)

(73) Assignee: KANEKA CORPORATION, Osaka (JP)

( * ) Notice: Subject to any disclaimer, the term of this patent is extended or adjusted under 35 U.S.C. 154(b) by 120 days.

(21) Appl. No.: 15/660,365

(22) Filed: Jul. 26, 2017

(65) Prior Publication Data

US 2018/0016306 A1   Jan. 18, 2018

Related U.S. Application Data

(63) Continuation of application No. PCT/JP2016/052038, filed on Jan. 25, 2016.

(30) Foreign Application Priority Data

Jan. 26, 2015 (JP) ................................. 2015-012664

(51) Int. Cl.
| | |
|---|---|
| *C07K 14/195* | (2006.01) |
| *C07K 14/315* | (2006.01) |
| *C07K 1/22* | (2006.01) |
| *C12N 15/09* | (2006.01) |
| *C07K 19/00* | (2006.01) |
| *G01N 33/53* | (2006.01) |
| *C12N 5/10* | (2006.01) |
| *C07K 16/00* | (2006.01) |
| *C07K 16/10* | (2006.01) |
| *C07K 17/00* | (2006.01) |

(52) U.S. Cl.
CPC .............. *C07K 14/195* (2013.01); *C07K 1/22* (2013.01); *C07K 14/315* (2013.01); *C07K 16/00* (2013.01); *C07K 16/1027* (2013.01); *C07K 17/00* (2013.01); *C07K 19/00* (2013.01); *C12N 5/10* (2013.01); *C12N 15/09* (2013.01); *G01N 33/53* (2013.01); *C07K 2317/55* (2013.01)

(58) Field of Classification Search
None
See application file for complete search history.

(56) References Cited

U.S. PATENT DOCUMENTS

| | | | |
|---|---|---|---|
| 5,143,844 A | 9/1992 | Abrahmsen et al. | |
| 5,965,390 A | 10/1999 | Bjorck et al. | |
| 6,162,903 A | 12/2000 | Trowern et al. | |
| 6,399,750 B1 | 6/2002 | Johansson | |
| 6,831,161 B1 | 12/2004 | Uhlen et al. | |
| 2002/0137918 A1* | 9/2002 | Gore ..................... | C07K 14/33 536/23.53 |
| 2003/0027283 A1 | 2/2003 | Bjorck et al. | |
| 2003/0153735 A1 | 8/2003 | Breece et al. | |
| 2005/0100970 A1 | 5/2005 | Uhlen et al. | |
| 2005/0143566 A1 | 6/2005 | Hober | |
| 2005/0215769 A1 | 9/2005 | Breece et al. | |
| 2006/0134805 A1 | 6/2006 | Berg et al. | |
| 2006/0142549 A1 | 6/2006 | Takeda et al. | |
| 2006/0194950 A1 | 8/2006 | Hober et al. | |
| 2006/0194955 A1 | 8/2006 | Hober et al. | |
| 2007/0178541 A1 | 8/2007 | Pedersen et al. | |
| 2007/0275873 A1 | 11/2007 | Heidner et al. | |
| 2010/0022760 A1 | 1/2010 | Hober et al. | |
| 2010/0286373 A1 | 11/2010 | Majima et al. | |

(Continued)

FOREIGN PATENT DOCUMENTS

| | | |
|---|---|---|
| CN | 1634990 A | 7/2005 |
| EP | 1123389 A1 | 8/2001 |

(Continued)

OTHER PUBLICATIONS

International Search Report issued in International Application No. PCT/JP2016/052036; dated Apr. 19, 2016 (2 pages).
International Search Report issued in International Application No. PCT/JP2017/015500; dated Jul. 18, 2017 (2 pages).
International Search Report issued in International Application No. PCT/JP2016/052038; dated Apr. 12, 2016 (2 pages).
Hober et al., ""Protein A chromatography for antibody purification"", Journal of Chromatography B, 848 (2007) pp. 40-47 (8 pages).
Shukla et al., ""Recent advances in large-scale production of monoclonal antibodies and related proteins"", Trends in Biotechnology, vol. 28, No. 5, pp. 253-261 (9 pages).
Nelson et al., ""Development trends for therapeutic antibody fragments"", Nature Biotechnology, vol. 27, No. 4, Apr. 2009, pp. 331-337 (7 pages).

(Continued)

*Primary Examiner* — Daniel E Kolker
*Assistant Examiner* — James L Rogers
(74) *Attorney, Agent, or Firm* — Osha Liang LLP

(57) ABSTRACT

A first immunoglobulin κ chain variable region-binding peptide includes an amino acid sequence of SEQ ID NO: 21 with substitution of one or more amino acid residues at the $15^{th}$ position, the $16^{th}$ position, the $17^{th}$ position or the $18^{th}$ position, wherein an acid dissociation pH thereof is shifted to a neutral side. A second immunoglobulin κ chain variable region-binding peptide further includes deletion, substitution and/or addition of 1-20 amino acid residues at positions other than the $15^{th}$ position, the $16^{th}$ position, the $17^{th}$ position and the $18^{th}$ position. A third immunoglobulin κ chain variable region-binding peptide includes an amino acid sequence with a sequence identity of 80% or more to the amino acid sequence of the first immunoglobulin κ chain variable region-binding peptide.

11 Claims, 3 Drawing Sheets
Specification includes a Sequence Listing."

(56) References Cited

U.S. PATENT DOCUMENTS

| | | |
|---|---|---|
| 2011/0112276 A1 | 5/2011 | Hober |
| 2011/0144311 A1 | 6/2011 | Chmielowski et al. |
| 2012/0238724 A1 | 9/2012 | Hober |
| 2013/0096276 A1 | 4/2013 | Yoshida et al. |
| 2013/0184438 A1 | 7/2013 | Hober et al. |
| 2013/0225796 A1 | 8/2013 | Takeda et al. |
| 2014/0018525 A1 | 1/2014 | Goklen et al. |
| 2014/0323695 A1 | 10/2014 | Takeda et al. |
| 2016/0024146 A1 | 1/2016 | Goklen et al. |
| 2016/0152668 A1 | 6/2016 | Hober |
| 2016/0237113 A1 | 8/2016 | Minakuchi |
| 2017/0159099 A1 | 6/2017 | Beam et al. |
| 2017/0174721 A1 | 6/2017 | Goklen et al. |
| 2017/0320919 A1* | 11/2017 | Rodrigo ............... C07K 14/195 |
| 2017/0334947 A1 | 11/2017 | Murata et al. |
| 2018/0036445 A1 | 2/2018 | Monie et al. |
| 2019/0144511 A1 | 5/2019 | Rodrigo et al. |

FOREIGN PATENT DOCUMENTS

| | | | |
|---|---|---|---|
| EP | 3153581 A1 | 4/2017 | |
| JP | H07506573 A | 7/1995 | |
| JP | H07507682 A | 8/1995 | |
| JP | 2006304633 A | 11/2006 | |
| JP | 2007252368 A | 10/2007 | |
| JP | 2008523140 A | 7/2008 | |
| JP | 2009/196998 A | 9/2009 | |
| JP | 2011/006489 A | 1/2011 | |
| JP | 2011-530606 A | 12/2011 | |
| JP | 2016079149 A | 5/2016 | |
| WO | 199717361 A1 | 5/1997 | |
| WO | 0015803 A1 | 3/2000 | |
| WO | 03080655 A1 | 10/2003 | |
| WO | 2005/033130 A2 | 4/2005 | |
| WO | 2005113584 A1 | 12/2005 | |
| WO | 2006126942 A1 | 11/2006 | |
| WO | WO-2007019376 A2 * | 2/2007 | ........... A61K 49/085 |
| WO | 2011118699 A1 | 9/2011 | |
| WO | 2012/135415 A1 | 10/2012 | |
| WO | 2014/141150 A1 | 9/2014 | |
| WO | 2015041218 A1 | 3/2015 | |
| WO | 2015190457 A1 | 12/2015 | |
| WO | 2015190458 A1 | 12/2015 | |
| WO | 2016031902 A1 | 3/2016 | |
| WO | 2016121701 A1 | 8/2016 | |

OTHER PUBLICATIONS

Bouvet, "Immunoglobulin Fab Fragment-Binding Proteins", Int. J. Immunopharmac., vol. 16, No. 5/6, 1994, pp. 419-424 (6 pages).

Kastern et al., "Structure of Peptostreptococcal Protein L and Identification of a Repeated Immunoglobulin Light Chain-binding Domain", The Journal of Biological Chemistry, vol. 267, No. 18, Jun. 25, 1992, pp. 12820-12825 (6 pages).

Murphy et al., "The functional units of a peptostreptococcal protein L", Molecular Microbiology, 1994, vol. 12, No. 6, pp. 911-920 (10 pages).

Housden et al., "Immunoglobulin-binding domains: Protein L from *Peptostreptococcus magnus*", Biochemical Society Transactions, 2003, vol. 31, Pt. 3, pp. 716-718 (3 pages).

Kihlberg et al., "Protein LG: A Hybrid Molecule with Unique Immunoglobulin Binding Properties", The Journal of Biological Chemistry, vol. 267, No. 35, Dec. 15, 1992, pp. 25583-25588 (6 pages).

Svensson et al., "Protein LA, a novel hybrid protein with unique single-chain Fv antibody- and Fab-binding properties", European Journal of Biochemistry, vol. 258, 1998, pp. 890-896 (7 pages).

Graille et al., "Complex between *Peptostreptococcus magnus* Protein L and a Human Antibody Reveals Structural Convergence in the Interaction Modes of Fab Binding Proteins", Structure, vol. 9, Aug. 2001, pp. 679-687 (9 pages).

Bottomley et al., "Cloning, expression and purification of Ppl-1, a kappa-chain binding protein, based upon protein L from *Peptostreptococcus magnus*", Bioseparation, vol. 5, 1995, pp. 359-367 (9 pages).

Capto (TM) L, Aug. 2014, [online] [retrieval date Apr. 11, 2016] <https://www.gelifesciences.com/gehcls_images/GELS/Related%20Content/Files/1346418936586/litdoc29010008_20141004004020.pdf> (8 pages).

Housden et al., "Observation and Characterization of the Interaction between a Single Immunoglobulin Binding Domain of Protein L and Two Equivalents of Human k Light Chains", The Journal of Biological Chemistry, vol. 279, No. 10, Mar. 5, 2004, pp. 9370-9378 (9 pages).

Tadeo et al., "Protein Stabilization and the Hofmeister Effect: The Role of Hydrophobic Solvation", Biophysical Journal, vol. 97, Nov. 2009, pp. 2595-2603 (9 pages).

Glyakina et al., "Mechanical stability analysis of the protein L immunoglobulin-binding domain by full alanine screening using molecular dynamics simulations", Biotechnology Journal, 2015, vol. 10, pp. 386-394 (11 pages).

Svensson et al., "Contributions of Amino Acid Side Chains to the Kinetics and Thermodynamics of the Bivalent Binding of Protein L to Ig k Light Chain", Biochemistry, 2004, vol. 43, pp. 2445-2457 (13 pages).

Millet et al., "The Effects of Mutations on Motions of Side-chains in Protein L Studied by 2H NMR Dynamics and Scalan Couplings", J. Mol. Biol., 2003, vol. 329, pp. 551-563 (13 pages).

Beckingham et al., "Interactions between a single immunoglobulin-binding domain of protein L from *Peptostreptococcus magnus* and a human k light chain", Biochem. J., 1999, vol. 340, pp. 193-199 (7 pages).

Yoshida et al., "Rational design and engineering of protein A to obtain the controlled elution profile in monoclonal antibody purification", Chem-Bio Informatics Journal, vol. 12, 2012, pp. 1-13 (13 pages).

Palmgren et al., "Improving the alkali stability of the kappa light chain-binding polypeptide from domain of *Peptostreptococcus* protein L", Abstracts of Papers, 251st ACS National Meeting & Exposition, Mar. 13, 2016 (Abstract) (1 page).

D. E. Kim et al. "A Breakdown of Symmetry in the Folding Transition State of Protein L", Journal of Molecular Biology, 2000, vol. 298, No. 5, pp. 971-984 (14 pages).

X. Yang et al. "Total chemical synthesis of the B1 domain of protein L from *Peptostreptococcus magnus*", Bioorganic Chemistry 2006, vol. 34, No. 3, pp. 131-141 (11 pages).

Extended European Search Report issued in European Application No. 16743306.9; dated Jun. 15, 2018 (8 pages).

M. Kastner, "Protein liquid chromatography," Journal of Chromatography Library, vol. 61, section 22.5.2, p. 811, 2000 (3 pages).

Office Action issued in U.S. Appl. No. 16/176,090; dated Oct. 1, 2019 (27 pages).

GE Healthcare Bio-Science AB, "Capto TM L"; Affinity chromatography; gelifesciences.com, Data file 29-0100-08 AC; (8 pages).

A. Murray et al, "Epitope Affinity Chromatography and Biophysical Studies of Monoclonal Antibodies and Recombinant Antibody Fragments", Journal of Chromatographic Science; Vol. 40, Jul. 2002; pp. 343-349 (7 pages).

B. R. Hubbard et al, "Vitamin K-dependent carboxylase: Affinity purification from bovine liver by using a synthetic propeptide containing the Y-carboxylation recognition site", Proceedings of the National Academy of Sciences of the United States of America; vol. 86, Sep. 1989; pp. 6893-6897 (6 pages).

International Search Report issued in International Application No. PCT/JP2017/016819, dated Jul. 25, 2017 (2 pages).

* cited by examiner

```
                                  (20)        (30)        (40)        (50)        (60)        (70)        (80)
                                    0          10          20          30          40          50          60
>PpL-312_B1:  KEETPETPETDSEEEVTIKANLIFANGSTQTAEFKGTFEKATSEAYAYADTLKKDNGEYTVDVADKGYTLNIKFAG-
>PpL-312_B2:  ---KEKTPE-EPKEEVTIKANLIYADGKTQTAEFKGTFEEATAEAYRYADALKKDNGEYTVDVADKGYTLNIKFAG-
>PpL-312_B3:  ---KEKTPE-EPKEEVTIKANLIYADGKTQTAEFKGTFEEATAEAYRYADLLAKENGKYTVDVADKGYTLNIKFAG-
>PpL-312_B4:  ---KEKTPE-EPKEEVTIKANLIYADGKTQTAEFKGTFAEATAEAYRYADLLAKENGKYTADLEDGGYTINIRFAG-
>PpL-312_B5:  ---KKVDEKPEEKEQVTIKENIYFEDGTVQTATFKGTFAEATAEAYRYADLLSKEHGKYTADLEDGGYTINIRFAG-
>PpL-3316_C1: ------KETPEPEEEVTIKANLIFADGSTQNAEFKGTFAKAVSDAYAYADALKKDNGEYTVDVADKGLTLNIKFAGK
>PpL-3316_C2: ---KEKPE-EPKEEVTIKVNLIFADGKTQTAEFKGTFEEATAKAYAYADLLAKENGEYTADLEDGGNTINIKFAG-
>PpL-3316_C3: -KETPETPE-EPKEEVTIKVNLIFADGKIQTAEFKGTFEEATAKAYAYANLLAKENGEYTADLEDGGNTINIKFAG-
>PpL-3316_C4: -KETPETPE-EPKEEVTIKVNLIFADGKTQTAEFKGTFEEATAEAYRYADLLAKVNGEYTADLEDGGYTINIKFAGK
```

MUTANT IMMUNOGLOBULIN κ CHAIN VARIABLE REGION-BINDING PEPTIDE

TECHNICAL FIELD

One or more embodiments of the present invention relate to an immunoglobulin κ chain variable region-binding peptide of which acid dissociation property to an immunoglobulin κ chain variable region is improved, an affinity separation matrix containing the peptide as a ligand, a method for producing an immunoglobulin κ chain variable region-containing protein by using the affinity separation matrix, a DNA encoding the peptide, a vector containing the DNA, and a transformant which is transformed by the vector.

BACKGROUND

As one of important functions of a protein, a capability to specifically bind to a specific molecule is exemplified. The function plays an important role in an immunoreaction and signal transduction in a living body. A technology utilizing the function for purifying a useful substance has been actively developed. As one example of proteins which are actually utilized industrially, for example, Protein A affinity separation matrix has been used for capturing an antibody drug to be purified with high purity at one time from a culture of an animal cell (Non-patent documents 1 and 2). Hereinafter, Protein A is abbreviated as "SpA" in some cases.

An antibody drug which has been developed is mainly a monoclonal antibody, and a monoclonal antibody has been produced on a large scale by using recombinant cell cultivation technology. A "monoclonal antibody" means an antibody obtained from a clone derived from a single antibody-producing cell. Most of antibody drugs launched presently are classified into an immunoglobulin G (IgG) in terms of a molecular structure. In addition, an antibody drug consisting of an antibody fragment has been actively subjected to clinical development. An antibody fragment is an antibody derivative having a molecular structure obtained by fragmenting IgG. A plurality of antibody drugs consisting of such a Fab fragment has been clinically developed (Non-patent Document 3).

In an initial purification step in an antibody drug production, the above-described SpA affinity separation matrix is utilized. However, SpA is basically a protein which specifically binds to a Fc region of IgG. Thus, SpA affinity separation matrix cannot capture an antibody fragment which does not contain a Fc region. Accordingly, an affinity separation matrix capable of capturing an antibody fragment which does not contain a Fc region of IgG is highly required industrially in terms of a platform development of a process for purifying an antibody fragment.

A plurality of peptides which can bind to a region except for a Fc region of IgG have been already known (Non-patent Document 4). Among such peptides, a peptide which can bind to a variable region, i.e. an antigen-binding domain, is the most preferred in terms of many kinds of an antibody fragment format to be bound and a capability to bind to IgM and IgA, and for example, Protein L is well-known as the peptide. Hereinafter, Protein L is abbreviated to "PpL". PpL is a protein which contains a plurality of κ chain variable region-binding domains. Hereinafter, a κ chain variable region is abbreviated as "VL-κ". In PpL, the amino acid sequences of each VL-κ-binding domain are different. The number of VL-κ-binding domains and the amino acid sequence of each VL-κ-binding domain are different depending on the kind of a strain. For example, the number of VL-κ-binding domains in PpL of *Peptostreptococcus magnus* 312 strain is five, and the number of VL-κ-binding domains in PpL of *Peptostreptococcus magnus* 3316 strain is four (Non-patent Documents 5 to 7, Patent Documents 1 and 2). The amino acid sequences of the above nine VL-κ-binding domains are different from each other.

A plurality of affinity separation matrices having PpL as a ligand have been commercially available. In the case of SpA, a protein engineering research to improve the function of SpA as a ligand for an affinity separation matrix by introducing a site-specific mutation has been actively advanced (Non-patent Document 1, Patent Documents 3 to 8). In the case of PpL, there are various reports of mutagenesis to academically analyze a binding force and a binding mode (Non-patent Documents 7 to 9), and there is also a report of a study to mutate the function of PpL as an affinity ligand (Patent Document 9). However, the report number on mutagenesis of PpL is smaller than that of SpA. In particular, with respect to the pH to elute an antibody which adsorbed on an affinity separation matrix by an acid, there are various reports that SpA can be eluted at the pH of 3.5 to 4.0 (Non-patent Document 1, Patent Documents 7 and 8); on the one hand, there is still room for improvement in the case of PpL.

Patent Document 1: JP H7-506573 T
Patent Document 2: JP H7-507682 T
Patent Document 3: U.S. Pat. No. 5,143,844 B
Patent Document 4: JP 2006-304633 A
Patent Document 5: EP 1123389 B
Patent Document 6: WO 03/080655
Patent Document 7: US 2006/0194950 A
Patent Document 8: WO 2011/118699
Patent Document 9: WO 00/15803
Non-patent Document 1: Hober S., et al., J. Chromatogr. B, 2007, vol. 848, pp. 40-47
Non-patent Document 2: Shukla A. A., et al., Trends Biotechnol., 2010, vol. 28, pp. 253-261
Non-patent Document 3: Nelson A. N., et al., Nat. Biotechnol., 2009, vol. 27, pp. 331-337
Non-patent Document 4: Bouvet P. J., Int. J. Immunopharmac., 1994, vol. 16, pp. 419-424
Non-patent Document 5: Kastern W., et al., J. Biol. Chem., 1992, vol. 267, pp. 12820-12825
Non-patent Document 6: Murphy J. P., et al., Mol. Microbiol., 1994, vol. 12, pp. 911-920
Non-patent Document 7: Housden N. G., et al., Biochemical Society Transactions, 2003, vol. 31, pp. 716-718
Non-patent Document 8: Housden N. G., et al., J. Biol. Chem., 2004, vol. 279, pp. 9370-9378
Non-patent Document 9: Tadeo X., et al., Biophys. J., 2009, vol. 97, pp. 2595-2603

As described above, various affinity separation matrixes to purify an immunoglobulin or a fragment thereof have been developed. In general, in order to purify an immunoglobulin or a fragment thereof by an affinity separation matrix, a neutral solution is contacted with an affinity separation matrix to selectively adsorb the immunoglobulin or fragment thereof, the matrix is washed to remove an impurity, and then the adsorbed immunoglobulin or fragment thereof is eluted by using an acidic eluate. In such a process, in order to obtain a target compound with high purity, it is needed to use an affinity separation matrix with high selective adsorbability and to sufficiently perform washing. In addition, in order to obtain a target compound with high collection rate, it is needed to conduct an elution in the range of acidic pH by which a selective adsorption can be certainly dissociated. However, an immunoglobulin or a fragment thereof as a target compound may suffer damage in a strong acidic condition.

SUMMARY

One or more embodiments of the present invention provide an immunoglobulin κ chain variable region-binding peptide which has an excellent selective adsorbability to a κ chain variable region peptide of an immunoglobulin but which can release the adsorbed κ chain variable region peptide by an acidic eluate with relatively high pH. Also, one or more embodiments of the present invention provide an affinity separation matrix containing the peptide as a ligand, a method for producing an immunoglobulin κ chain variable region-containing protein by using the affinity separation matrix, a DNA encoding the peptide, a vector containing the DNA, and a transformant which is transformed by the vector.

The inventor found that when an affinity separation matrix containing Protein L (PpL) as a ligand is preliminarily evaluated, there is a large difference between chromatography profiles depending on the kind of an antibody fragment although the light chain is κ chain. Specifically, a stronger acid tends to be required when an antibody fragment which is hardly leaked during an intermediate washing due to high coupling capacitance is eluted. The present inventor designed a molecular of a mutant of a κ chain variable region-binding domain of PpL, prepared the mutant from a transformant using a protein engineering means and a genetic engineering means, and compared the properties of the prepared mutants. As a result, the present inventor completed one or more embodiments of the present invention by introducing a specific mutation into a κ chain variable region-binding domain of Protein L derived from *Peptostreptococcusl magnus*.

Hereinafter, one or more embodiments of the present invention is described.

[1] An immunoglobulin κ chain variable region-binding peptide, being any one of the following (1) to (3):

(1) an immunoglobulin κ chain variable region-binding peptide having an amino acid sequence corresponding to an amino acid sequence of SEQ ID NO: 21 with substitution of one or more amino acid residues at positions selected from the 15$^{th}$ position, the 16$^{th}$ position, the 17$^{th}$ position and the 18$^{th}$ position ("first immunoglobulin κ chain variable region-binding peptide"), wherein an acid dissociation pH thereof is shifted to a neutral side in comparison with an acid dissociation pH before introducing the substitution;

(2) an immunoglobulin κ chain variable region-binding peptide having an amino acid sequence specified in the (1) with a mutation of deletion, substitution and/or addition of 1 or more and 20 or less amino acid residues in a region except for the 15$^{th}$ position, the 16$^{th}$ position, the 17$^{th}$ position and the 18$^{th}$ position ("second immunoglobulin κ chain variable region-binding peptide"), wherein an acid dissociation pH thereof is shifted to a neutral side in comparison with an acid dissociation pH before introducing the mutation;

(3) an immunoglobulin κ chain variable region-binding peptide having an amino acid sequence with a sequence identity of 80% or more to the amino acid sequence specified in the (1) ("third immunoglobulin κ chain variable region-binding peptide"), wherein an acid dissociation pH thereof is shifted to a neutral side in comparison with an acid dissociation pH before introducing the mutation, provided that the amino acid residue substitution specified in the (1) at one or more positions selected from the 15$^{th}$ position, the 16$^{th}$ position, the 17$^{th}$ position and the 18$^{th}$ position is not further mutated in (3).

[2] The immunoglobulin κ chain variable region-binding peptide according to the above [1], wherein the amino acid sequence specified in the (1) is one of the amino acid sequences of SEQ ID NOs: 12 to 20.

[3] The immunoglobulin κ chain variable region-binding peptide according to the above [1], wherein the amino acid residue at the 16$^{th}$ position or the 18$^{th}$ position is substituted in the amino acid sequence specified in the (1).

[4] The immunoglobulin κ chain variable region-binding peptide according to any one of the above [1] to [3], wherein the 15$^{th}$ position is substituted by His, the 16$^{th}$ position is substituted by Ala, Asp or His, the 17$^{th}$ position is substituted by His, and the 18$^{th}$ position is substituted by Asp, Gln or His in the amino acid sequence specified in the (1).

[5] The immunoglobulin κ chain variable region-binding peptide according to any one of the above [1] to [4], wherein a position of the deletion, substitution and/or addition of the amino acid residue is N-terminal and/or C-terminal in the amino acid sequence specified in the (2).

[6] The immunoglobulin κ chain variable region-binding peptide according to any one of the above [1] to [5], wherein the sequence identity is 95% or more in the amino acid sequence specified in the (3).

[7] An immunoglobulin κ chain variable region-binding peptide multimer, comprising two or more domains formed by connecting two or more of the immunoglobulin κ chain variable region-binding peptides according to any one of the above [1] to [6].

[8] An affinity separation matrix, wherein the immunoglobulin κ chain variable region-binding peptide according to any one of the above [1] to [6] or the immunoglobulin κ chain variable region-binding peptide multimer according to the above [7] is immobilized on a water-insoluble carrier as a ligand.

[9] A method for producing a protein comprising an immunoglobulin κ chain variable region, comprising the steps of:

contacting the affinity separation matrix according to the above [8] with a liquid sample comprising the protein comprising the immunoglobulin κ chain variable region; and separating the protein comprising the immunoglobulin κ chain variable region bound on the affinity separation matrix from the affinity separation matrix.

[10] A DNA, encoding the immunoglobulin κ chain variable region-binding peptide according to any one of the above [1] to [6] or the immunoglobulin κ chain variable region-binding peptide multimer according to the above [7].

[11] A vector, comprising the DNA according to the above [10].

[12] A transformant, transformed by the vector according to the above [11].

The affinity separation matrix prepared by immobilizing the κ chain variable region-binding peptide according to one or more embodiments of the present invention on an insoluble carrier has excellent selective adsorbability to a κ chain variable region-containing protein of an immunoglobulin. On the one hand, the affinity separation matrix also has an excellent acid dissociation property as a conflicting property. The term "excellent acid dissociation property" means that κ chain variable region-containing protein is dissociated in an acidic condition closer to neutrality for elution and an elution peak profile when a κ chain variable region-containing protein is eluted in an acidic condition is sharper. When an elution peak of chromatography is sharper, an eluate which contains an antibody with high concentration and of which volume is smaller can be obtained.

BRIEF DESCRIPTION OF THE DRAWINGS

FIG. 1 represents an alignment of amino acid sequences of VL-κ-binding domains derived from PpL.

DETAILED DESCRIPTION OF THE EMBODIMENTS

Figure 2:
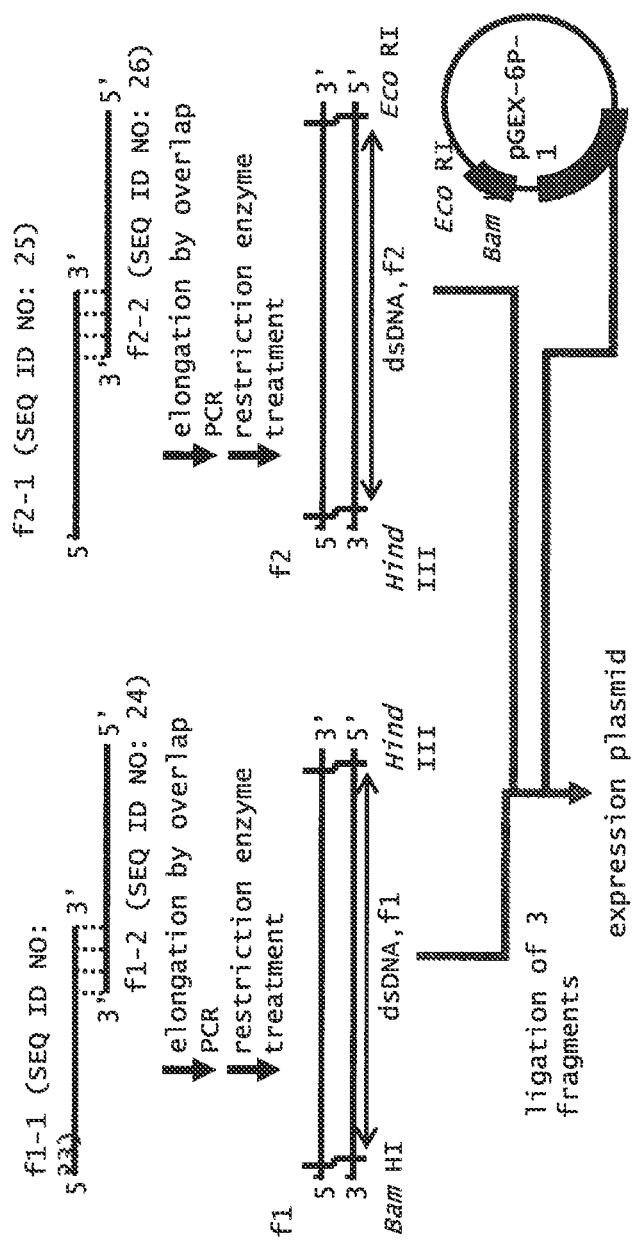
FIG. 2 represents a method for preparing an expression plasmid of LB5t-Wild.1d.

One or more embodiments of the present invention relate to the immunoglobulin κ chain variable region-binding peptide selected from the following (1) to (3):

(1) an immunoglobulin κ chain variable region-binding peptide having an amino acid sequence corresponding to an amino acid sequence of SEQ ID NO: 21 with substitution of one or more amino acid residues at positions selected from the $15^{th}$ position, the $16^{th}$ position, the $17^{th}$ position and the $18^{th}$ position ("first immunoglobulin κ chain variable region-binding peptide"), wherein an acid dissociation pH thereof is shifted to a neutral side in comparison with an acid dissociation pH before introducing the substitution;

(2) an immunoglobulin κ chain variable region-binding peptide having an amino acid sequence specified in the (1) with a mutation of deletion, substitution and/or addition of 1 or more and 20 or less amino acid residues in a region except for the $15^{th}$ position, the $16^{th}$ position, the $17^{th}$ position and the $18^{th}$ position ("second immunoglobulin κ chain variable region-binding peptide"), wherein an acid dissociation pH thereof is shifted to a neutral side in comparison with an acid dissociation pH before introducing the mutation;

(3) an immunoglobulin κ chain variable region-binding peptide having an amino acid sequence with a sequence identity of 80% or more to the amino acid sequence specified in the (1) ("third immunoglobulin κ chain variable region-binding peptide"), wherein an acid dissociation pH thereof is shifted to a neutral side in comparison with an acid dissociation pH before introducing the mutation, provided that the amino acid residue substitution specified in the (1) at one or more positions selected from the $15^{th}$ position, the $16^{th}$ position, the $17^{th}$ position and the $18^{th}$ position is not further mutated in (3).

An "immunoglobulin (IgG)" is a glycoprotein produced by a B cell of a lymphocyte and has a function to recognize a molecule such as a specific protein to be bound. An immunoglobulin has not only a function to specifically bind to a specific molecule, i.e. antigen, but also a function to detoxify and remove an antigen-containing factor in cooperation with other biological molecule or cell. An immunoglobulin is generally referred to as "antibody", and the name is inspired by such functions. All of immunoglobulins basically have the same molecular structure. The basic structure of an immunoglobulin is a Y-shaped four-chain structure consisting of two light chains and two heavy chains of polypeptide chains. A light chain (L chain) is classified into two types of λ chain and κ chain, and all of immunoglobulins have either of the chains. A heavy chain (H chain) is classified into five types of γ chain, μ chain, α chain, δ chain and ε chain, and an immunoglobulin is classified into isotypes depending on the kind of a heavy chain. An immunoglobulin G (IgG) is a monomer immunoglobulin, is composed of two heavy chains (γ chains) and two light chains, and has two antigen-binding sites.

A lower half vertical part in the "Y" shape of an immunoglobulin is referred to as a "Fc region", and an upper half "V" shaped part is referred to as a "Fab region". A Fc region has an effector function to initiate a reaction after an antibody binds to an antigen, and a Fab region has a function to bind to an antigen. A Fab region and Fc region of a heavy chain are bound to each other through a hinge part. Papain, which is a proteolytic enzyme and which is contained in *papaya*, decomposes a hinge part to cut into two Fab regions and one Fc region. The part close to the tip of the "Y" shape in a Fab region is referred to as a "variable region (V region)", since there are various changes in the amino acid sequence in order to bind to various antigens. A variable region of a light chain is referred to as a "VL region", and a variable region of a heavy chain is referred to as a "VH region". A Fc region and the other part in a Fab region except for a V region are referred to as a "constant region (C region)", since there is relatively less change. A constant region of a light chain is referred to as a "CL region", and a constant region of a heavy chain is referred to as a "CH region". A CH region is further classified into three regions of CH1 to CH3. A Fab region of a heavy chain is composed of a VH region and CH1, and a Fc region of a heavy chain is composed of CH2 and CH3. There is a hinge part between CH1 and CH2. Protein L binds to a variable region of which a light chain is κ chain (Non-patent Documents 5 to 7), and the variable region is sometimes abbreviate to "VL-κ" in the present disclosure.

The κ chain variable region-binding peptide according to one or more embodiments of the present invention binds to a κ chain variable region of an immunoglobulin. A VL-κ chain variable region-containing protein to which the peptide according to one or more embodiments of the present invention binds may contain a κ chain variable region of an immunoglobulin, and may be IgG containing both of a Fab region and a Fc region, other Ig such as IgM, IgD and IgA, or an immunoglobulin derivative prepared by mutating such Ig using protein engineering. Such an immunoglobulin molecule derivative to be bound by the VL-κ chain variable region-binding peptide according to one or more embodiments of the present invention is not particularly restricted as long as the derivative contains a VL-κ chain variable region. For example, the derivative is exemplified by a Fab fragment which is fragmented to only a Fab region of an immunoglobulin G, scFv consisting of only a variable region of an immunoglobulin G, a chimera immunoglobulin G prepared by replacing a part of domains of a human immunoglobulin G with a domain of an immunoglobulin G derived from other organism to be fused, an immunoglobulin G of which a sugar chain in a Fc region is subjected to molecular alteration, and a scFv fragment to which a drug covalently binds.

In one or more embodiments of the present invention, the term "peptide" means any molecules having a polypeptide structure. In the range of the "peptide", not only a so-called protein but also a fragmented peptide and a peptide to which other peptide is bound through a peptide bond are included. The term "domain" means a unit of higher-order structure of a protein. A domain is composed of from dozens to hundreds of amino acid residues, and means a peptide unit which can sufficiently serve some kind of a physicochemical or biochemical function. The term "mutant" of a protein or peptide means a protein or peptide obtained by introducing at least one substitution, addition or deletion of an amino acid into a sequence of a wild protein or peptide. A mutation to substitute an amino acid is described by adding a wild or non-mutated amino acid residue before the number of a substituted position and adding a mutated amino acid residue after the number of the substituted position. For example, the mutation to substitute Gly at $29^{th}$ position by Ala is described as G29A.

Protein L (PpL) is a protein derived from a cell wall of an anaerobic gram-positive coccus classified in *Peptostreptococcus*. PpL may be derived from *Peptostreptococcusl magnus*, and two kinds of PpL derived from *Peptostreptococcusl magnus* 312 and *Peptostreptococcusl magnus* 3316 may be used; however, PpL is not restricted thereto (Non-patent Documents 4 to 6). In the present disclosure, PpL derived from *Peptostreptococcusl magnus* 312 is sometimes abbreviated to "PpL312" and PpL derived from *Peptostreptococcusl magnus* 3316 is sometimes abbreviated to "PpL3316". The amino acid sequence of PpL312 is SEQ ID NO: 1, and the amino acid sequence of PpL3316 is SEQ ID NO: 2, which SEQ ID NOs contain a signal sequence.

PpL contains a plurality of VL-κ-binding domains consisting of 70 to 80 residues. The number of VL-κ-binding domains in PpL312 is 5, and the number of VL-κ-binding domains in PpL3316 is 4. Each of VL-κ-binding domains of PpL312 are referred to as B1 domain (SEQ ID NO: 3), B2 domain (SEQ ID NO: 4), B3 domain (SEQ ID NO: 5), B4 domain (SEQ ID NO: 6) and B5 domain (SEQ ID NO: 7) in the order from the N-terminal, and each of VL-κ-binding domains of PpL3316 are referred to as C1 domain (SEQ ID NO: 8), C2 domain (SEQ ID NO: 9), C3 domain (SEQ ID NO: 10) and C4 domain (SEQ ID NO: 11) in the order from the N-terminal.

FIG. 1 shows the alignment of the amino acid sequences of the various VL-κ-binding domains. In FIG. 1, the residue number in accordance with Non-patent Documents 7 and 8 and Patent Document 9 is described in the parentheses. It has been found from a research that about 20 residues at the N-terminal part do not form a specific secondary structure; and even when the N-terminal region is deleted, the three-dimensional structure and the VL-κ binding property of a VL-κ-binding domain is maintained (Non-patent Document 7). As a result, for example, peptides having the amino acid sequence of SEQ ID NO: 12 with respect to B1 domain, the amino acid sequence of SEQ ID NO: 13 with respect to B2 domain, the amino acid sequence of SEQ ID NO: 14 with respect to B3 domain, the amino acid sequence of SEQ ID NO: 15 with respect to B4 domain, the amino acid sequence of SEQ ID NO: 16 with respect to B5 domain, the amino acid sequence of SEQ ID NO: 17 with respect to C1 domain, the amino acid sequence of SEQ ID NO: 18 with respect to C2 domain, the amino acid sequence of SEQ ID NO: 19 with respect to C3 domain and the amino acid sequence of SEQ ID NO: 20 with respect to C4 domain function as a VL-κ-binding domain. The amino acid sequence of the B5 domain of PpL312 in the present disclosure may be SEQ ID NO: 16. The amino acid sequence used in one or more embodiments of the present invention may be the amino acid sequence of SEQ ID NO: 21, which exhaustively contains the amino acid residues common to the above-described domains (SEQ ID NOs: 12 to 20). In the present disclosure, an amino acid residue number is given on the presumption that the N-terminal residue of SEQ ID NO: 21 is the $1^{st}$ position. In FIG. 1, residue numbers are described in accordance with the above-described definition, and the residues from Val at the $1^{st}$ position of the above-described domains (SEQ ID NOs: 12 to 20) through Ala at the $60^{th}$ position are described in boldface.

In one or more embodiments of the present invention, the specific substitution mutation is introduced in the of VL-κ-binding domains B1 to B5 and C1 to C4 of wild PpL; as a result, the pH to dissociate a protein containing an immunoglobulin κ chain variable region by an acid is shifted to a neutral side in comparison with that before the introduction of the mutation.

As experimentally demonstrated in Examples described later, a κ chain variable region peptide is dissociated from the mutant VL-κ chain variable region-binding peptide (1) in an acidic condition with higher pH for elution; and when a κ chain variable region peptide is eluted in an acidic condition, an elution peak is sharper.

In one or more embodiments, the substitution position of an amino acid residue is one or more amino acid residues at the positions selected from the $15^{th}$ position, the $16^{th}$ position, the $17^{th}$ position and the $18^{th}$ position of the amino acid sequence of SEQ ID NO: 21. For example, in SEQ ID NO: 12, the $15^{th}$ position is Gln, the $16^{th}$ position is Thr, the $17^{th}$ position is Ala and the $18^{th}$ position is Glu. In the amino acid sequences of SEQ ID NOs: 12 to 20, the $15^{th}$ position is Gln and the $17^{th}$ position is Ala. The $16^{th}$ position of the amino acid sequence of C1 domain (SEQ ID NO: 17) is Asn, and the $18^{th}$ position of B5 domain (SEQ ID NO: 16) is Thr. Even when the numbers of amino acids in the amino acid sequences before and after the introduction of the mutation are different, a skilled person can easily identify the position corresponding to from the $15^{th}$ position through the $18^{th}$ position of SEQ ID NO: 21 under the condition that the sequence identity is 80% or more. Specifically, the position can be confirmed by aligning the sequences using a program for amino acid sequence multiple alignment: Clustal (http://www.clustal.org/omega/) or gene information processing software: GENETYX (https://www.genetyx.co.jp/). The position of the amino acid residue to be substituted in one or more embodiments of the present invention corresponds to the $35^{th}$ position through the $38^{th}$ position on the basis of the residue number described in Non-patent Documents 7 and 8 and Patent Document 9.

The mutant VL-κ chain variable region-binding peptide (1) according to one or more embodiments of the present invention has the amino acid sequence in which the above-described one or more amino acid residues at positions selected from the $15^{th}$ position, the $16^{th}$ position, the $17^{th}$ position and the $18^{th}$ position are substituted. The position to be substituted may be the $15^{th}$ position, the $16^{th}$ position, the $17^{th}$ position and the $18^{th}$ position, may be the $15^{th}$ position, the $16^{th}$ position and the $18^{th}$ position, may be the $16^{th}$ position and the $18^{th}$ position, or may be the $16^{th}$ position.

In one or more embodiments of the present invention, the phrase, a peptide "has a (specific) amino acid sequence", means that the specific amino acid sequence is contained in the amino acid sequence of the peptide and the function of the peptide is maintained. The sequence of a peptide other than a specific amino acid sequence is exemplified by histidine tag, a linker sequence for immobilization, and a crosslinking structure such as —S—S— bond.

The kind of an amino acid for mutation is not particularly restricted, the mutation may be a substitution by a non-protein-constituting amino acid and a non-natural amino acid, and a natural amino acid may be used in terms of genetic engineering production. A natural amino acid is classified into the categories of a neutral amino acid; an acidic amino acid such as Asp and Glu; and a basic amino acid such as Lys, Arg and His. A neutral amino acid is classified into the categories of an aliphatic amino acid; an imino acid such as Pro; and an aromatic amino acid such as Phe, Tyr and Trp. An aliphatic amino acid is classified into the categories of Gly; Ala; a branched amino acid such as Val, Leu and Ile; a hydroxy amino acid such as Ser and Thr; a sulfur-containing amino acid such as Cys and Met; and an acid amide amino acid such as Asn and Gln. Since Tyr has a phenolic hydroxyl group, Tyr may be classified into not only an aromatic amino acid but also a hydroxy amino acid. From another viewpoint, a natural amino acid may also be classified into the categories of a nonpolar amino acid with high hydrophobicity, such as Gly, Ala, Val, Leu, Ile, Trp, Cys, Met, Pro and Phe; a neutral polar amino acid such as Asn, Gln, Ser, Thr and Tyr; an acidic polar amino acid such as Asp and Glu; and a basic polar amino acid such as Lys, Arg and His. In addition, His, Asp and Glu may be used, since the amino acids has a functional group which can be protonated in an acidic condition.

The amino acid at the $15^{th}$ position may be substituted by Ala, Glu or His, or by His. The amino acid at the $16^{th}$ position may be substituted by Ala, Asp, Gly, Ile, Leu or His, or by Ala, Asp or His. The amino acid at the $17^{th}$ position may be substituted by Glu or His, or by His. The amino acid at the $18^{th}$ position may be substituted by Asp, Gln or His.

The mutant VL-κ chain variable region-binding peptide (2) has the amino acid sequence specified in the above-described (1) with deletion, substitution and/or addition of 1 or more and 20 or less amino acid residues in a region except for the $15^{th}$ position, the $16^{th}$ position, the $17^{th}$ position and the $18^{th}$ position, wherein an acid dissociation pH thereof is shifted to a neutral side in comparison with an acid dissociation pH before introducing the mutation.

The number of the mutation of the above-described deletion, substitution and/or addition may be not more than 15 or not more than 10, not more than 7, not more than 5 or not more than 3, 1 or 2, or 1. In the amino acid sequence of the mutant immunoglobulin κ chain variable region-binding peptide (2) according to one or more embodiments of the present invention, the position of the deletion, substitution and/or addition of the amino acid residue is not particularly restricted as long as the position is not the $15^{th}$ position, the $16^{th}$ position, the $17^{th}$ position and the $18^{th}$ position specified in the mutant VL-κ chain variable region-binding peptide (1). The position of the deletion, substitution and/or addition of the amino acid residue is exemplified by N-terminal and/or C-terminal. The terminal positions may be as the position of the deletion and/or addition.

The amino acid sequences of SEQ ID NOs: 12 to 21 corresponds to the amino acid sequences of SEQ ID Nos: 3 to 11 with deletion of 10 to 20 residues at the N-terminal and 1 to 2 residues at the C-terminal. Accordingly, the amino acid sequence to be added to the N-terminal and/or C-terminal is exemplified by the above-described amino acid sequence at the N-terminal and/or C-terminal. As one embodiment, the amino acid sequence to be added to the N-terminal is exemplified by Glu-Glu or Glu-Gln. As one embodiment, the amino acid sequence to be added to the C-terminal is exemplified by Gly, Cys or Gly-Cys.

The mutant VL-κ chain variable region-binding peptide (3) has an amino acid sequence with a sequence identity of 80% or more to the amino acid sequence specified in the above-described (1), and an acid dissociation pH thereof is shifted to a neutral side in comparison with an acid dissociation pH before introducing the mutation, provided that the amino acid residue substitution specified in the above-described (1) at one or more positions selected from the $15^{th}$ position, the $16^{th}$ position, the $17^{th}$ position and the $18^{th}$ position is not further mutated in (3).

The mutant VL-κ chain variable region-binding peptide (3) according to one or more embodiments of the present invention has an amino acid sequence with a sequence identity of 80% or more to the amino acid sequence specified in the above-described (1), and the pH to dissociate an immunoglobulin κ chain variable region-containing protein is shifted to a neutral side in comparison with the pH before introducing the mutation, provided that the amino acid residue substitution specified in the above-described (1) at one or more positions selected from the $15^{th}$ position, the $16^{th}$ position, the $17^{th}$ position and the $18^{th}$ position is not further mutated in (3).

The above-described sequence identity may be 85% or more, not less than 90%, not less than 95%, not less than 98% or not less than 99%, or 99.5% or more. The sequence identity can be evaluated by a program for amino acid sequence multiple alignment, such as Clustal (http://www-.clustal.org/omega/), as described above.

The mutant VL-κ chain variable region-binding peptides (1) to (3) according to one or more embodiments of the present invention are characterized in that the pH to dissociate an immunoglobulin κ chain variable region (VL-κ)-containing protein by an acid is shifted to a neutral side in comparison with an acid dissociation pH before introducing the mutation. In general, the connection between peptides is lost in a strong acidic condition and a strong basic condition by the change of the charge on a molecular surface and the change of the steric structure due to a denaturation. The term "acid dissociation pH" means a pH at which the specific connection is lost at an acid side, i.e. when a pH value is less than 7, leading to dissociation. In other words, the acid dissociation pH means the highest pH to dissociate and elute an adsorbed VL-κ-containing protein from an affinity separation matrix having the mutant VL-κ chain variable region-binding peptides (1) to (3) according to one or more embodiments of the present invention as a ligand. In the present disclosure, an acid dissociation pH and an acid elution pH basically have the same meaning. The phrase "an acid dissociation pH is shifted to a neutral side in comparison with an acid dissociation pH before introducing the mutation" means that the value of the pH necessary for dissociation of the connection is smaller before the mutation and larger after the mutation. In other words, the connection can be dissociated by using a weaker acidic solution after the mutation.

It is difficult to unambiguously determine the value range of the acid dissociation pH, since the value is changed depending on the kind of a VL-κ-containing protein, the kind and concentration of a buffer component in an acidic solution; and with respect to an affinity separation matrix, the value also is changed depending on the kind and structure of a water-insoluble carrier and the kind and structure of a linker for immobilizing a ligand. In general, the acid dissociation pH before introducing the mutation is about 2.0 or more and about 3.5 or less; on the one hand, the pH after introducing the mutation according to one or more embodiments of the present invention is not restricted but is shifted to about 3.0 or more and about 4.5 or less. When an elution is carried out in such a condition, the adsorbed antibody can be eluted with less damage (chose S., et al., Biotechnology and bioengineering, 2005, vol. 92, no. 6). When the mutation according to one or more embodiments of the present invention is introduced, the acid dissociation pH may be shifted by 0.1 or more to the neutral side, the pH may be shifted by 0.2 or more to the neutral side, the pH may be shifted by 0.3 or more to the neutral side, the pH may be shifted by 0.4 or more to the neutral side, and the pH may be shifted by 0.5 or more to the neutral side.

The method for measuring the acid dissociation pH before and after introducing the mutation is not restricted as long as the interaction between biomolecules can be evaluated by the method. For example, the pH can be measured by a biosensor such as Biacore system (GE Healthcare) utilizing a surface plasmon resonance principle. As a method for measuring the acid dissociation pH, for example, one peptide to be interacted is immobilized on a sensor tip, a solution of another peptide having an adjusted pH is added into a flow channel, it is evaluated whether a binding signal is detected or not, and the pH at which a binding signal is not detected is specified; but the method is not restricted thereto. As another method, a buffer solution having an adjusted pH is added after a peptide solution, and then a change of binding signals due to the remaining peptide without dissociation before and after the addition may be evaluated. With respect to a measurement condition, a temperature is maintained at a range between 20 and 40° C. and the pH is adjusted to be neutral between 5 and 8 when a binding condition is observed. A component of a buffer solution is exemplified by phosphoric acid, tris(hydroxymethyl)aminomethane, bis[tris(hydroxymethyl)aminomethane] in the case of a neutral buffer and by acetic acid, citric acid and glycine in the case of an acidic buffer, but is not restricted thereto. The concentration of NaCl in a buffer solution is not particularly restricted, and may be about 0 to 0.15 M, or 0 M when a dissociation condition is observed. In the above-described evaluation, it is important to equalize the conditions other than the mutation in order to compare the difference before and after the mutation. For example, when Biacore system is used for the evaluation, the mutant VL-κ chain variable region-binding peptide may be immobilized on a chip as a solid phase or may be added in a flow channel as a liquid phase, and the evaluation is possible in both cases. For example, when it is difficult to adjust the amount of the mutant VL-κ chain variable region-binding peptide to be constant, the concentration of the mutant VL-κ chain variable region-binding peptide to be added to the flow channel may be adjusted when the peptide is added to the flow channel.

As a method for evaluating the acid dissociation pH, a method for evaluating a chromatography profile with using an affinity separation matrix. For example, one peptide to be bound is immobilized on a column for chromatography, the column is connected to a chromatography device, a solution of another peptide is added into the column, pH of an eluent is gradually reduced with a linear gradient to elute the adsorbed peptide, and the pH corresponding to the top peak of the eluted peptide is specified, but the method is not restricted thereto. The temperature, buffer and salt concentration during the measurement may be adjusted as the above, but are not restricted thereto. For example, the components of a buffer A for association and a buffer B for dissociation may be the same for clear linear gradient other than pH. It is important in the measurement to uniform all of the conditions except for the mutation in order to compare the difference before and after the mutation. Also, in the evaluation method, the mutant VL-κ chain variable region-binding peptide may be immobilized on a column as a solid phase or may be added to be eluted as a liquid phase, and the evaluation is possible in both cases. For example, when it is difficult to adjust the amount of the mutant VL-κ chain variable region-binding peptide which is immobilized on a column, the concentration of the mutant VL-κ chain variable region-binding peptide to be added into the column may be adjusted and the obtained chromatography profiles are overlapped to be compared.

The mutant VL-κ chain variable region-binding peptides (1) to (3) according to one or more embodiments of the present invention can be immobilized on a column as an affinity ligand and have an excellent VL-κ-binding capability. For example, an affinity for a VL-κ chain variable region can be evaluated by a biosensor such as Biacore system (GE Healthcare Bioscience) using a surface plasmon resonance principle.

A binding parameter is exemplified by an affinity constant ($K_A$) and a dissociation constant ($K_D$) (Nagata et al., "Real-time analysis experiment of biomaterial interactions", Springer-Verlag Tokyo, 1998, page 41). The affinity constant corresponds to a value obtained by dividing a binding rate constant ($k_{on}$) by a dissociation rate constant ($k_{off}$), in other words, $K_A = k_{on}/k_{off}$.

An affinity constant between the VL-κ chain variable region-binding peptide according to one or more embodiments of the present invention and a VL-κ chain variable region-containing peptide can be measured by using Biacore system, specifically by immobilizing the VL-κ chain variable region-containing peptide on a sensor tip and adding the VL-κ chain variable region-binding peptide according to one or more embodiments of the present invention to be flown into a channel in the conditions of 25° C. and pH 7.4. An affinity constant $K_A$ between the peptide having the mutated sequence according to one or more embodiments of the present invention and a VL-κ chain variable region-containing peptide may be $1 \times 10^6$ $M^{-1}$ or more, $5 \times 10^6$ $M^{-1}$ or more, or $1 \times 10^7$ $M^{-1}$ or more; however, such an affinity constant is not restricted to the above-described values, since an affinity constant is varied depending on the kind of a VL-κ chain variable region-containing peptide and the number of domains of VL-κ chain-binding peptide.

PpL is a protein which contains 4 or 5 VL-κ chain variable region-binding domains in the form of tandem line. As one of the embodiments, the VL-κ chain variable region-binding peptide according to one or more embodiments of the present invention may be a multimer of 2 or more monomers or single domains of the VL-κ chain variable region-binding peptide connected each other. The number of the monomers or single domains may be 3 or more, 4 or more, or 5 or more. With respect to the upper limit of the number of connected domains, the number may be 10 or less, 8 or less, or 6 or less. Such a multimer may be a homomultimer in which one kind of VL-κ chain variable region-binding peptides are connected, such as homodimer and homotrimer, or a heteromultimer in which two or more kinds of VL-κ chain variable region-binding peptides are connected, such as heterodimer and heterotrimer, on the proviso that the heteromer does not contain any one of B1 to B4 domain of PpL312 and C1 to C4 domain of PpL3316.

A method for connection in a VL-κ chain variable region-binding peptide multimer according to one or more embodiments of the present invention is exemplified by a connecting method through one or more amino acid residues and a directly connecting method without an amino acid residue, but is not restricted thereto. The number of the amino acid residue for connection is not particularly restricted, and may be 20 residues or less, 15 residues or less, 10 residues or less, 5 residues or less, or 2 residues or less. The amino acid residue for connection may not destabilize a three dimensional structure of a monomer protein.

As one of the embodiments, a fusion peptide characterized in that the VL-κ chain variable region-binding peptide or a multimer thereof according to one or more embodiments of the present invention is fused with other peptide having a different function as one component is exemplified. A fusion peptide is exemplified by a peptide fused with albumin or glutathione S-transferase, i.e. GST, but is not restricted to the examples. In addition, peptides fused with a nucleic acid such as DNA aptamer, a drug such as an antibiotic or a polymer such as PEG, i.e. polyethylene glycol, are also included in the range of one or more embodiments of the present invention as long as the availability of the peptide of one or more embodiments of the present invention is utilized in a fusion peptide.

In one or more embodiments of the present invention, the peptide may be used as an affinity ligand which is characterized in having an affinity for an immunoglobulin or a fragment thereof, particularly a VL-κ chain variable region. An affinity separation matrix obtained by immobilizing the ligand on a water-insoluble carrier is also similarly included in one or more embodiments of the present invention.

The affinity separation matrix according to one or more embodiments of the present invention is characterized in that the above-described immunoglobulin κ chain variable region-binding peptide and the above-described immunoglobulin κ chain variable region-binding peptide multimer according to one or more embodiments of the present invention is immobilized on a water-insoluble carrier as a ligand.

The term "ligand" in one or more embodiments of the present invention means a substance and a functional group to selectively bind to or adsorb a target molecule from an aggregate of molecules on the basis of a specific affinity between molecules, such as binding between an antigen and an antibody, and means the peptide which specifically binds to an immunoglobulin in one or more embodiments of the present invention. In one or more embodiments of the present invention, the term "ligand" also means an "affinity ligand".

The term "affinity ligand" in one or more embodiments of the present invention means a substance and a functional group to selectively bind to or adsorb a target molecule from an aggregate of molecules on the basis of a specific affinity between molecules, such as binding between an antigen and an antibody, and means the peptide which specifically binds to an immunoglobulin in one or more embodiments of the present invention. In one or more embodiments of the present invention, the term "ligand" also means an "affinity ligand".

A water-insoluble carrier usable in one or more embodiments of the present invention is exemplified by an inorganic carrier such as glass beads and silica gel; an organic carrier composed of a synthetic polymer such as cross-linked polyvinyl alcohol, cross-linked polyacrylate, cross-linked polyacrylamide and cross-linked polystyrene or a polysaccharide such as crystalline cellulose, cross-linked cellulose, cross-linked agarose and cross-linked dextran; and a composite carrier obtained from the combination of the above carriers, such as an organic-organic composite carrier and an organic-inorganic composite carrier. The commercial product thereof is exemplified by porous cellulose gel GCL2000, Sephacryl S-1000 prepared by crosslinking allyl dextran and methylene bisacrylamide through a covalent bond, an acrylate carrier Toyopearl, a cross-linked agarose carrier Sepharose CL4B, and a cross-linked cellulose carrier Cellufine. However, it should be noted that the water-insoluble carrier usable in one or more embodiments of the present invention is not restricted to the carriers exemplified as the above.

The water-insoluble carrier usable in one or more embodiments of the present invention may have large surface area and that the carrier is porous with a large number of fine pores having a suitable size in terms of a purpose and method for using the affinity separation matrix according to one or more embodiments of the present invention. The carrier may have any form such as beads, monolith, fiber and film (including hollow fiber), and any form can be selected.

The above-described ligand is covalently immobilized on the above-described water-insoluble carrier directly or through a linker group. The linker group is exemplified by a $C_{1-6}$ alkylene group, an amino group (—NH—), an ether group (—O—), a carbonyl group (—C(=O)—), an ester group (—C(=O)O— or —OC(=O)—), an amide group (—C(=O) NH— or —NHC(=O)—), a urea group (—NHC(=O)NH—); a group formed by connecting 2 or more and 10 or less groups selected from the group consisting of a $C_{1-6}$ alkylene group, an amino group, an ether group, a carbonyl group, an ester group, an amide group and a urea group; a $C_{1-6}$ alkylene group having a group selected from the group consisting of an amino group, an ether group, a carbonyl group, an ester group, an amide group and a urea group on one or both of ends. The above-described number of the connected groups may be 8 or less or 6 or less, 5 or less, or 4 or less. The above-described $C_{1-6}$ alkylene group may be substituted by a substituent such as a hydroxy group.

The affinity separation matrix according to one or more embodiments of the present invention can be produced by immobilizing the above-described ligand on the above-described water-insoluble carrier.

With respect to a method for immobilizing the ligand, for example, the ligand can be bound to a carrier by a conventional coupling method utilizing an amino group, a carboxy group or a thiol group of the ligand. Such a coupling method is exemplified by an immobilization method including activation of a carrier by a reaction with cyanogen bromide, epichlorohydrin, diglycidyl ether, tosyl chloride, tresyl chloride, hydrazine, sodium periodate or the like, or introduction of a reactive functional group on the carrier surface, and the coupling reaction between the resulting carrier and a compound to be immobilized as a ligand; and an immobilization method by condensation and crosslinking which method includes adding a condensation reagent such as carbodiimide or a reagent having a plurality of functional groups in the molecule, such as glutaraldehyde, into a mixture containing a carrier and a compound to be immobilized as a ligand.

A spacer molecule composed of a plurality of atoms may be introduced between the ligand and carrier. Alternatively, the ligand may be directly immobilized on the carrier. Accordingly, the VL-κ chain variable region-binding peptide according to one or more embodiments of the present invention may be chemically modified for immobilization, or may have an additional amino acid residue useful for immobilization. Such an amino acid useful for immobilization is exemplified by an amino acid having a functional group useful for a chemical reaction for immobilization in a side chain, and specifically exemplified by Lys having an amino group in a side chain and Cys having a thiol group in a side chain. Since the binding capability of the peptide according to one or more embodiments of the present invention to a VL-κ chain variable region is principally maintained in a matrix prepared by immobilizing the peptide as a ligand in one or more embodiments of the present invention, any modification and change for immobilization are included in the range of one or more embodiments of the present invention.

It becomes possible by using the affinity separation matrix according to one or more embodiments of the present invention that a protein containing a κ chain variable region of an immunoglobulin G, i.e. VL-κ-containing protein, is purified in accordance with affinity column chromatography purification method. A peptide containing a VL-κ-containing protein can be purified by a procedure in accordance with a method for purifying an immunoglobulin by affinity column chromatography, for example, such as a method using SpA affinity separation matrix (Non-Patent Document 1).

Specifically, after a solution which contains a VL-κ-containing protein and of which pH is approximately neutral is prepared, the solution is allowed to pass through an affinity column packed with the affinity separation matrix according to one or more embodiments of the present invention so that the VL-κ-containing protein is adsorbed. Then, an appropriate amount of a pure buffer is allowed to pass through the affinity column to wash the inside of the column. At the time, the target VL-κ-containing protein is still adsorbed on the affinity separation matrix according to one or more embodiments of the present invention in the column. The affinity separation matrix on which the peptide according to one or more embodiments of the present invention is immobilized as a ligand is excellent in the absorption and retention performance of a target VL-κ-containing protein from the step of adding a sample through the step of washing the matrix. Then, an acid buffer of which pH is appropriately adjusted is allowed to pass through the column to elute the target VL-κ-containing protein. As a result, purification with high purity can be achieved. Into the acid buffer used for eluting the peptide, a substance for promoting dissociation from the matrix may be added.

In particular, when the affinity separation matrix according to one or more embodiments of the present invention is used, an acid buffer of which pH is closer to neutrality can be used as an eluate. The pH value of the acid buffer to be used may be 3.0 or more, 3.1 or more, 3.2 or more, 3.3 or more, 3.4 or more, 3.5 or more, 3.6 or more, 3.7 or more, or 3.8 or more. The upper limit of the pH value of an acid buffer to be used is not particularly restricted; and when washing is carried out during an affinity chromatography using a washing solution having a pH of about 5.0 and an incubation is carried out at a pH of about 3.8 to remove virus after the purification, the pH value of an acid buffer to be used may be 4.5 or less, or 4.0 or less.

The affinity separation matrix according to one or more embodiments of the present invention can be reused by allowing an adequate strong acid or strong alkaline pure buffer which do not completely impair the function of the ligand compound or the base material of the carrier to pass through the matrix for washing. In the buffer for reuse, an adequate modifying agent or an organic solvent may be added.

One or more embodiments of the present invention also relate to a DNA encoding the above-described mutant VL-κ chain variable region-binding peptide. The DNA encoding the peptide according to one or more embodiments of the present invention may be any DNA as long as the amino acid sequence produced from translation of the base sequence of the DNA constitutes the peptide. Such a base sequence can be obtained by common known techniques, for example, using polymerase chain reaction (hereinafter, abbreviated as "PCR") technology. Alternatively, such abase sequence can be synthesized by publicly-known chemical synthesis techniques or is available from DNA libraries. A codon in the base sequence may be substituted by a degenerate codon, and the base sequence is not necessarily the same as the original base sequence as long as the translated amino acids are the same as those encoded by the original base sequence. It is possible to obtain a recombinant DNA having the one or more base sequences, a vector containing the recombinant DNA, such as a plasmid or a phage, a transgenic microorganism or cell transformed by the vector having the DNA, a genetically engineered organisms having the DNA introduced therein, or a cell-free protein synthesis system using the DNA as a template for transcription.

The VL-κ chain variable region-binding peptide according to one or more embodiments of the present invention may be obtained as a fusion peptide fused with a publicly-known protein which beneficially has an action to assist the expression of the protein or to facilitate the purification of the protein. In other words, it is possible to obtain a microorganism or cell containing at least one recombinant DNA encoding a fusion peptide containing the VL-κ chain variable region-binding peptide according to one or more embodiments of the present invention. The above-described protein is exemplified by a maltose-binding protein (MBP) and a glutathione S-transferase (GST), but is not restricted to the exemplified proteins.

Site-specific mutagenesis for modifying the DNA encoding the peptide according to one or more embodiments of the present invention can be carried out using recombinant DNA technology, PCR method or the like as follows.

A mutagenesis by recombinant DNA technology can be carried out as follows: in the case where there are suitable restriction enzyme recognition sequences on both sides of a target mutagenesis site in the gene encoding the peptide according to one or more embodiments of the present invention, cassette mutagenesis method can be carried out in which method a region containing the target mutagenesis site is removed by cleaving the restriction enzyme recognition sites with the above-described restriction enzymes and then a mutated DNA fragment is inserted. Into the mutated DNA fragment, mutation is introduced only at the target site by a method such as chemical synthesis.

For example, site-directed mutagenesis by PCR can be carried out by double primer mutagenesis. In double primer mutagenesis, PCR is carried out by using a double-stranded plasmid encoding the peptide according to one or more embodiments of the present invention as a template, and using two kinds of synthesized oligo primers which contain complementary mutations in the +strand and −strand.

A DNA encoding a multimer peptide can be produced by ligating the desired number of DNAs each encoding the monomer peptide (single domain) according to one or more embodiments of the present invention to one another in tandem. For example, with respect to a connecting method for the DNA encoding the multimer peptide, a suitable restriction enzyme site is introduced in the DNA sequence and double-stranded DNA fragments cleaved with a restriction enzyme are ligated using a DNA ligase. One restriction enzyme site may be introduced or a plurality of restriction enzyme sites of different types may be introduced. When the base sequences encoding each monomer peptide in the DNA encoding the multimer peptide are the same, homologous recombination may be possibly induced in a host. Thus, the sequence identity between base sequences of DNAs encoding the monomer peptides to be connected may be 90% or less, 85% or less, 80% or less, or 75% or less. The identity of a base sequence can be also determined by an ordinary method similarly to an amino acid sequence.

The "expression vector" according to one or more embodiments of the present invention includes a base sequence encoding the above-described peptide according to one or more embodiments of the present invention or a part of the amino acid sequence of the peptide, and a promoter that can be operably linked to the base sequence to function in a host. Usually, the vector can be constructed by linking or inserting a gene encoding the peptide according to one or more embodiments of the present invention to a suitable vector. The vector for insertion of the gene is not particularly restricted as long as the vector is capable of autonomous replication in a host. As such a vector, a plasmid DNA or a phage DNA can be used. For example, in the case of using *Escherichia coli* as a host, a pQE series vector (manufactured by QIAGEN), a pET series vector (manufactured by Merck), a pGEX series vector (manufactured by GE Healthcare Bioscience) or the like can be used.

The transformant according to one or more embodiments of the present invention can be produced by introducing the recombinant vector according to one or more embodiments of the present invention into a host cell. A method for introducing the recombinant DNA into a host is exemplified by a method using a calcium ion, electroporation method, spheroplast method, lithium acetate method, *agrobacterium* infection method, particle gun method and polyethyleneglycol method, but is not restricted thereto. A method for expressing the function of the obtained gene in a host is also exemplified by a method in which the gene according to one or more embodiments of the present invention is implanted into a genome (chromosome). A host cell is not particularly restricted, and bacteria (eubacteria) such as *Escherichia coli, Bacillus subtilis, Brevibacillus, Staphylococcus, Streptococcus, Streptomyces* and *Corynebacterium* may be used in terms of mass production in a low cost.

The VL-κ chain variable region-binding peptide according to one or more embodiments of the present invention can be produced by culturing the above-described transformant in a medium, allowing the transformant to express and accumulate the peptide according to one or more embodiments of the present invention in the cultured bacterial cell (including the periplasmic space of the bacterial cell) or in the culture medium (outside the bacterial cell), and collecting the desired peptide from the culture. Further, the peptide according to one or more embodiments of the present invention can also be produced by culturing the above-described transformant in a medium, allowing the transformant to express and accumulate the fusion protein containing the peptide according to one or more embodiments of the present invention in the cultured bacterial cell (including the periplasmic space of the bacterial cell) or in the culture medium (outside the bacterial cell), collecting the fusion peptide from the culture, cleaving the fusion peptide with a suitable protease, and collecting the desired peptide.

The transformant according to one or more embodiments of the present invention can be cultured in a medium in accordance with a common method for culturing a host cell. The medium used for culturing the obtained transformant is not particularly restricted as long as the medium enables high yield production of one or more embodiments of the present invention peptide with high efficiency. Specifically, carbon source and nitrogen source, such as glucose, sucrose, glycerol, polypeptone, meat extract, yeast extract and casamino acid can be used. In addition, an inorganic salt such as potassium salt, sodium salt, phosphate, magnesium salt, manganese salt, zinc salt and iron salt is added as required. In the case of an auxotrophic host cell, a nutritional substance necessary for the growth thereof may be added. In addition, an antibiotic such as penicillin, erythromycin, chloramphenicol and neomycin may be added as required.

Furthermore, in order to inhibit the degradation of the target peptide caused by a host-derived protease present inside or outside the bacterial cell, a publicly-known protease inhibitor and/or other commercially available protease inhibitor may be added in an appropriate concentration. The publicly-known protease inhibitor is exemplified by phenylmethane sulfonyl fluoride (PMSF), benzamidine, 4-(2-aminoethyl)-benzenesulfonyl fluoride (AEBSF), antipain, chymostatin, leupeptin, Pepstatin A, phosphoramidon, aprotinin and ethylenediaminetetraacetic acid (EDTA).

In order to obtain rightly folded VL-κ chain variable region-binding peptide according to one or more embodiments of the present invention, for example, a molecular chaperone such as GroEL/ES, Hsp70/DnaK, Hsp90 and Hsp104/C1pB may be used. For example, such a molecular chaperone is co-existed with the peptide according to one or more embodiments of the present invention by coexpression or as a fusion protein. As a method for obtaining rightly folded peptide according to one or more embodiments of the present invention, addition of an additive for assisting right folding into the medium and culturing at a low temperature are exemplified, but the method is not restricted thereto.

The medium for culturing transformant produced from an *Escherichia coli* as a host is exemplified by LB medium containing triptone 1%, yeast extract 0.5% and NaCl 1%, 2xYT medium containing triptone 1.6%, yeast extract 1.0% and NaCl 0.5%, or the like.

For example, the transformant may be aerobically cultured in an aeration-stirring condition at a temperature of 15 to 42° C., or 20 to 37° C., for from several hours to several days. As a result, the peptide according to one or more embodiments of the present invention is accumulated in the cultured cell (including the periplasmic space of the cell) or in the culture liquid (outside the cell) to be recovered. In some cases, the culturing may be performed anaerobically without aeration. In the case where a recombinant peptide is secreted, the produced recombinant peptide can be recovered after the culture period by separating the supernatant containing the secreted peptide using a common separation method such as centrifugation and filtration from the cultured cell. In addition, in the case where the peptide is accumulated in the cultured cell (including the periplasmic space), the peptide accumulated in the cell can be recovered, for example, by collecting the bacterial cell from the culture liquid by centrifugation, filtration or the like, and then disrupting the bacterial cell by sonication method, French press method or the like, and/or solubilizing the bacterial cell by adding a surfactant or the like.

A method for purifying the peptide according to one or more embodiments of the present invention can be carried out by any one or an appropriate combination of techniques such as affinity chromatography, cation or anion exchange chromatography, gel filtration chromatography and the like. It can be confirmed whether the obtained purified substance is the target peptide or not by an ordinary method such as SDS polyacrylamide gel electrophoresis, N-terminal amino acid sequence analysis and Western blot analysis.

The present application claims the benefit of the priority date of Japanese patent application No. 2015-12664 filed on Jan. 26, 2015. All of the contents of the Japanese patent application No. 2015-12664 filed on Jan. 26, 2015, are incorporated by reference herein.

EXAMPLES

Hereinafter, one or more embodiments of the present invention are described in more detail with Examples.

However, one or more embodiments of the present invention is not restricted to the following Examples.

The mutant peptide obtained in the following Examples is described as "peptide name—introduced mutation", and wild type into which mutation is not introduced is described as "peptide name—Wild". For example, β5 domain of wild PpL312 having SEQ ID NO: 7 is described as "LB5-Wild". In the following Examples, B5 domain of PpL312 having SEQ ID NO: 16 was mainly used in the experiments and is described as "LB5t-Wild" so that the domain can be distinguished from that having SEQ ID NO: 7. Mutant B5 domain of PpL312 into which mutation of T16H was introduced is described as "LB5t-T16H". With respect to a mutant having kinds of mutations, the mutations are described together with a slash. For example, mutant B5 domain of PpL312 into which mutations of T16H and T18D were introduced is described as "LB5t-T16H/T18D". The number of domain is put down with "d" after a period. For example, a mutant consisting of one domain is described as "LB5t-T16H.1d".

Example 1: Preparation of Various Mutant VL-κ-Binding Peptides in PpL (1) Preparation of Expression Plasmids A base sequence of SEQ ID NO: 22 encoding the peptide having the amino acid sequence of LB5t-Wild.1d (SEQ ID NO: 16) was designed by reverse translation from the amino acid sequence. For experimental reasons, the base sequence was designed so that the base sequence encoded an amino acid sequence having Glu-Gln at the N-terminal and Gly at the C-terminal. Such added sequences of 1 to 2 residues can be observed in B5 domain of wild PpL. The method for producing the expression plasmid is shown in FIG. 2. A DNA encoding LB5t-Wild.1d was prepared by ligating two kinds of double-stranded DNAs (f1 and f2) having the same restriction enzyme site, and integrated into the multiple cloning site of an expression vector. In fact, the preparation of the peptide-coding DNA and the integration into the vector were simultaneously performed by ligating three fragments for connecting three double-stranded DNAs of the two kinds of double-stranded DNAs and an expression vector. The two kinds of double-stranded DNAs were prepared by elongating two kinds of single-stranded DNAs (f1-1/f1-2 or f2-1/f2-2) respectively containing about 30-base complementary region with overlapping PCR. Hereinafter, the specific experimental procedure is described. Single-stranded oligo DNAs f1-1 (SEQ ID NO: 23)/f1-2 (SEQ ID NO: 24) were synthesized by outsourcing to Sigma Genosys. The overlapping PCR was performed using Pyrobest (manufactured by Takara Bio, Inc.) as a polymerase. The PCR product was subjected to agarose electrophoresis and the target band was cut out to extract the double-stranded DNA. The thus extracted double-stranded DNA was cleaved with the restriction enzymes BamHI and HindIII (both available from Takara Bio, Inc.). Similarly, single-stranded oligo DNAs f2-1 (SEQ ID NO: 25)/f2-2 (SEQ ID NO: 26) were synthesized by outsourcing. The double-stranded DNA synthesized by overlapping PCR was extracted and cleaved with the restriction enzymes HindIII and EcoRI (both available from Takara Bio, Inc.). Then, the two kinds of double-stranded DNAs were sub-cloned into the BamHI/EcoRI site in the multiple cloning site of a plasmid vector pGEX-6P-1 (GE Healthcare Bioscience). The ligation reaction for the subcloning was performed using Ligation high (manufactured by TOYOBO CO., LTD.) in accordance with the protocol attached to the product.

A competent cell ("*Escherichia coli* HB101" manufactured by Takara Bio, Inc.) was transformed using the above-described plasmid vector pGEX-6P-1 in accordance with the protocol attached to the competent cell product. By using the plasmid vector pGEX-6P-1, LB5t-Wild.1d which was fused with glutathione-S-transferase (hereinafter, abbreviated as "GST") could be produced. Then, the plasmid DNA was amplified and extracted using a plasmid purification kit ("Wizard Plus SV Minipreps DNA Purification System" manufactured by Promega) in accordance with the standard protocol attached to the kit. The base sequence of the peptide-coding DNA of the expression plasmid was determined by using a DNA sequencer ("3130x1 Genetic Analyzer" manufactured by Applied Biosystems). The sequencing PCR was performed by using a gene analysis kit ("BigDye Terminator v.1.1 Cycle Sequencing Kit" manufactured by Applied Biosystems) and DNA primers for sequencing the plasmid vector pGEX-6P-1 (manufactured by GE Healthcare Bioscience) in accordance with the attached protocol. The sequencing product was purified by using a plasmid purification kit ("BigDye XTerminator Purification Kit" manufactured by Applied Biosystems) in accordance with the attached protocol and used for the base sequence analysis.

Also, with respect to DNAs encoding various LB5t mutants, a double-stranded DNA corresponding f1 of FIG. 2 was synthesized by PCR using the prepared expression plasmid of LB5t-Wild.1d as a template, a DNA primer for 5'-side sequencing of plasmid vector pGEX-6P-1 and each 3'-side DNA primer of SEQ ID NOs: 27 to 34. The PCR using the primers was conducted using Blend Taq-Plus— (TOYOBO CO., LTD.) in accordance with the enclosed protocol. The double-stranded DNA was cleaved using restriction enzymes BamHI and HindIII, and the expression plasmid of KB5t-Wild.1d was also cleaved using the same restriction enzymes. The cleaved DNA and plasmid were ligated to prepare expression vectors of various LB5t mutants. The SEQ ID NO of the base sequence of oligo DNA, base sequence of cDNA encoding the mutant and the amino acid sequence of the mutant are shown in Table 1.

TABLE 1

| Mutant | Primer DNA | Encoding DNA | Amino acid |
| --- | --- | --- | --- |
| LB5t-Q15H.1d | 27 | 35 | 43 |
| LB5t-T16A.1d | 28 | 36 | 44 |
| LB5t-T16D.1d | 29 | 37 | 45 |
| LB5t-T16H.1d | 30 | 38 | 46 |
| LB5t-A17H.1d | 31 | 39 | 47 |
| LB5t-T18D.1d | 32 | 40 | 48 |
| LB5t-T18H.1d | 33 | 41 | 49 |
| LB5t-T18Q.1d | 34 | 42 | 50 |

(2) Production and Purification of Protein

The transformant produced by integrating each of the mutant LB5t gene obtained in the above-described (1) was cultured in 2xYT medium containing ampicillin at 37° C. overnight. The culture solution was inoculated in 2xYT medium containing about 100-fold amount of ampicillin for cultivation at 37° C. for about 2 hours. Then, isopropyl-1-thio-β-D-galactoside, which is hereinafter abbreviated to IPTG, was added so that the final concentration thereof became 0.1 mM, and the transformant was further cultured at 37° C. for 18 hours.

After the cultivation, the bacterial cell was collected by centrifugation and re-suspended in 5 mL of PBS buffer. The cell was broken by sonication and centrifuged to separate a supernatant fraction as a cell-free extract and an insoluble fraction. When a target gene is integrated into the multiple cloning site of pGEX-6P-1 vector, a fusion peptide having GST added to the N-terminal is produced. Each fraction was analyzed by SDS electrophoresis; as a result, a peptide band assumed to be induced by IPTG was detected at a position corresponding to a molecular weight of about 25,000 or more in the cases of each of all the cell-free extracts obtained from all of the cultured solutions of each transformant.

The GST fusion peptide was roughly purified from each of the cell-free extract containing the GST fusion peptide by affinity chromatography using a GSTrap FF column (GE Healthcare Bioscience), which had an affinity for GST. Specifically, each of the cell-free extract was added to the GSTrap FF column and the column was washed with a standard buffer (20 mM $NaH_2PO_4$—$Na_2HPO_4$, 150 mM NaCl, pH 7.4). Then, the target GST fusion peptide was eluted by using an elution buffer (50 mM Tris-HCl, 20 mM Glutathione, pH 8.0).

When a gene is integrated into the multiple cloning site of pGEX-6P-1 vector, an amino acid sequence by which GST can be cleaved using sequence-specific protease: PreScission Protease (manufactured by GE Healthcare Bioscience) is inserted between GST and a target protein. By using such PreScission Protease, GST was cleaved in accordance with the attached protocol. The target peptide was purified by gel filtration chromatography using a Superdex 75 10/300 GL column (manufactured by GE Healthcare Bioscience) from the GST-cleaved sample used for assay. Each of the reaction mixture was added to the Superdex 75 10/300 GL column equilibrated with a standard buffer, and the target protein therein was separated and purified from the cleaved GST and PreScission Protease. The above-described all of the peptide purification by chromatography using the column were performed by using AKTAprime plus system (manufactured by GE Healthcare Bioscience). In addition, after the cleavage of GST, the sequence of Gly-Pro-Leu-Gly-Ser derived from the vector pGEX-6P-1 was added at the N-terminal side of the protein produced in the present example. For example, LB55-T36H.1d had an amino acid sequence of SEQ ID NO: 46 with Gly-Pro-Leu-Gly-Ser-Glu-Gln at the N-terminal side and Gly at the C-terminal side.

Example 2: Evaluation of Affinity of Various LB5t Mutants for aRSV-Fab (1) Preparation of Fab Fragment Derived from IgG A humanized monoclonal IgG product as a raw material was fragmented into a Fab fragment and a Fc fragment using papain, and only the Fab fragment was separated and purified. Specifically, anti-RSV monoclonal IgG product (generic name: "Palivizumab", product name: "Synagis" manufactured by AbbVie Inc.), of which light chain is κ chain, was dissolved in a buffer for papain treatment (0.1 M AcOH—AcONa, 2 mM EDTA, 1 mM cysteine, pH 5.5), and agarose on which papain was immobilized ("Papain Agarose from *papaya* latex" manufactured by SIGMA) was added thereto. The mixture was incubated with stirring by a rotator at 37° C. for about 8 hours. The IgG-Fab was purified by recovering as a flow-through fraction in an affinity chromatography using MabSelect SuRe column (manufactured by GE Healthcare Bioscience) from the reaction mixture which contained both of a Fab fragment and a Fc fragment and which was separated from the agarose on which papain was immobilized. The obtained IgG-Fab solution was subjected to purification by gel filtration chromatography using Superdex 75 10/300 GL column to obtain the solution of IgG-Fab (aRSV-Fab). In the chromatography, a standard buffer was used for equilibration and separation. Similarly to the above-described Example 1, AKTAprime plus system was used in the chromatography for protein purification.

(2) Analysis of Affinity of Various LB5t Mutants for IgG-Fab

The affinity of each of the various LB5t mutants obtained in the above Example 1 (2) for IgG-Fab was evaluated using a biosensor Biacore 3000 (manufactured by GE Healthcare Bioscience) utilizing surface plasmon resonance. In the present example, the IgG-Fab obtained in the above Example 2 (1) was immobilized on a sensor tip, and each of the peptide was flown on the tip to detect the interaction between the two. The IgG-Fab was immobilized on a sensor tip CM5 by amine coupling method using N-hydroxysuccinimide (NHS) and N-ethyl-N'-(3-dimethylaminopropyl) carbodiimide hydrochloride (EDC), and ethanolamine was used for blocking. All of the sensor tip and reagents for immobilization were manufactured by GE Healthcare Bioscience. The IgG-Fab solution was diluted about 10 times using a buffer for immobilization (10 mM $CH_3COOH$—$CH_3COONa$, pH 4.5), and the IgG-Fab was immobilized on the sensor tip in accordance with the protocol attached to the Biacore 3000. In addition, a reference cell as negative control was also prepared by activating another flow cell on the tip with EDC/NHS and then immobilizing human serum albumin (manufactured by Wako Pure Chemical Industries, Ltd.). Peptide solutions of each of the various LB5t mutants having concentrations of 0.01, 0.1, 1 or 10 μM were prepared using a running buffer (20 mM $NaH_2PO_4$—$Na_2HPO_4$, 150 mM NaCl, 0.005% P-20, pH 7.4). The peptide solution was added to the sensor tip in a flow rate of 40 μL/min for 1 minute. Bonding response curves at the time of addition (association phase, for 1 minute) and after the addition (dissociation phase, for 1 minute) were sequentially obtained at a measurement temperature of 25° C. After each measurement, the cells were washed using about 20 mM NaOH. The bonding response curve obtained by subtracting the bonding response curve of the reference cell was subjected to fitting analysis by a binding model of 1:1 using a software BIA evaluation attached to the system, and affinity constant ($K_A = k_{on}/k_{off}$) to aRSC-Fab was calculated. The result is shown in Table 2 with each binding parameter of LB5t-Wild.1d, which parameter was measured in Comparative Example 2.

TABLE 2

| | LB5t-Wild.1d | | |
|---|---|---|---|
| | $k_{on}$ ($\times 10^5$ [$M^{-1}s$]) | $k_{off}$ ($\times 10^{-2}$ [$s^{-1}$]) | $K_A$ ($\times 10^6$ [$M^{-1}$]) |
| LB5t-Wild.1d | 1.85 | 1.48 | 12.5 |
| LB5t-Q15H.1d | 3.25 | 4.85 | 6.7 |
| LB5t-T16A.1d | 4.21 | 2.25 | 18.71 |
| LB5t-T16D.1d | 3.81 | 2.65 | 14.38 |
| LB5t-T16H.1d | 4.28 | 1.59 | 26.92 |
| LB5t-A17H.1d | 0.8 | 7.38 | 1.08 |
| LB5t-T18D.1d | 3.17 | 4.67 | 6.79 |
| LB5t-T18H.1d | 4.22 | 3.6 | 11.72 |
| LB5t-T18Q.1d | 3.73 | 2.96 | 12.6 |

As the result shown in Table 2, for example, when the mutations of T16A, T16D, T16H, T18H and T18Q were introduced, the affinity constant $K_A$ of the mutant for aRSV-Fab became about 1 time to 2 times in comparison with the value of the wild type before introducing the mutations. The result indicated that VL-κ binding capability was maintained. With respect to the mutations of Q15H, A17H and T18D, the affinity constant $K_A$ was decreased but the values were $1 \times 10^6$ M$^{-1}$ or more. The VL-κ binding capability of $1 \times 10^6$ M$^{-1}$ or more is considered to be sufficient, since a ligand may adsorb and keep a target molecule in a column and excessively high binding capability may not be suitable for an elution.

Example 3: Measurement of Acid Dissociation pH Between Various LV5t Mutants and aRSV-Fab (1) Preparation of Fab Fragment-Immobilized Carrier An affinity separation matrix on which aRSV-Fab obtained in the above Example 2 was immobilized was prepared by using a commercially available coupling column for immobilizing a ligand. The column has an amino group as a functional group for coupling.

As a water-insoluble carrier, 1 mL of a commercially available prepacked column ("Hitrap NHS activated HP" manufactured by GE Healthcare Bioscience) was used. The column contains a crosslinked agarose as a base material and an amino group is introduced as an active functional group for immobilizing a protein ligand, and a ligand was immobilized in accordance with the product manual. Specifically, 2 mL of ice-cooled 1 mM HCl was flown at a rate of 1 mL/min repeatedly three times to remove isopropanol in the column.

Then, 1 mL of a 1 mg/mL aRSV-Fab solution in a coupling buffer (0.2 M NaHCO$_3$, 0.5 M NaCl, pH8.3) was immediately flown at the same rate. The top and bottom of the column were stoppled, and the column was stood still at 25° C. for 30 minutes to immobilize the obtained ligand in the column.

Then, the column was opened, and 3 mL of the coupling buffer was flown at the same rate to recover the unreacted aRSV-Fab. Next, 2 mL of a blocking buffer (0.5 M ethanolamine, 0.5 M NaCl, pH8.3) was flown repeatedly three times and 2 mL of a washing buffer (0.1 M acetic acid, 0.5 M NaCl, pH4.0) was flown three times.

Each of the above-described procedure to flow the blocking buffer and washing buffer were performed three times one after the other. Finally, 2 mL of a standard buffer (20 mM NaH$_2$PO$_4$—Na$_2$HPO$_4$, 150 mM NaCl, pH7.4) was flown to complete the preparation of an affinity separation matrix.

(2) Chromatography Experiment Using Fab Fragment-Immobilized Carrier

Figure 3:
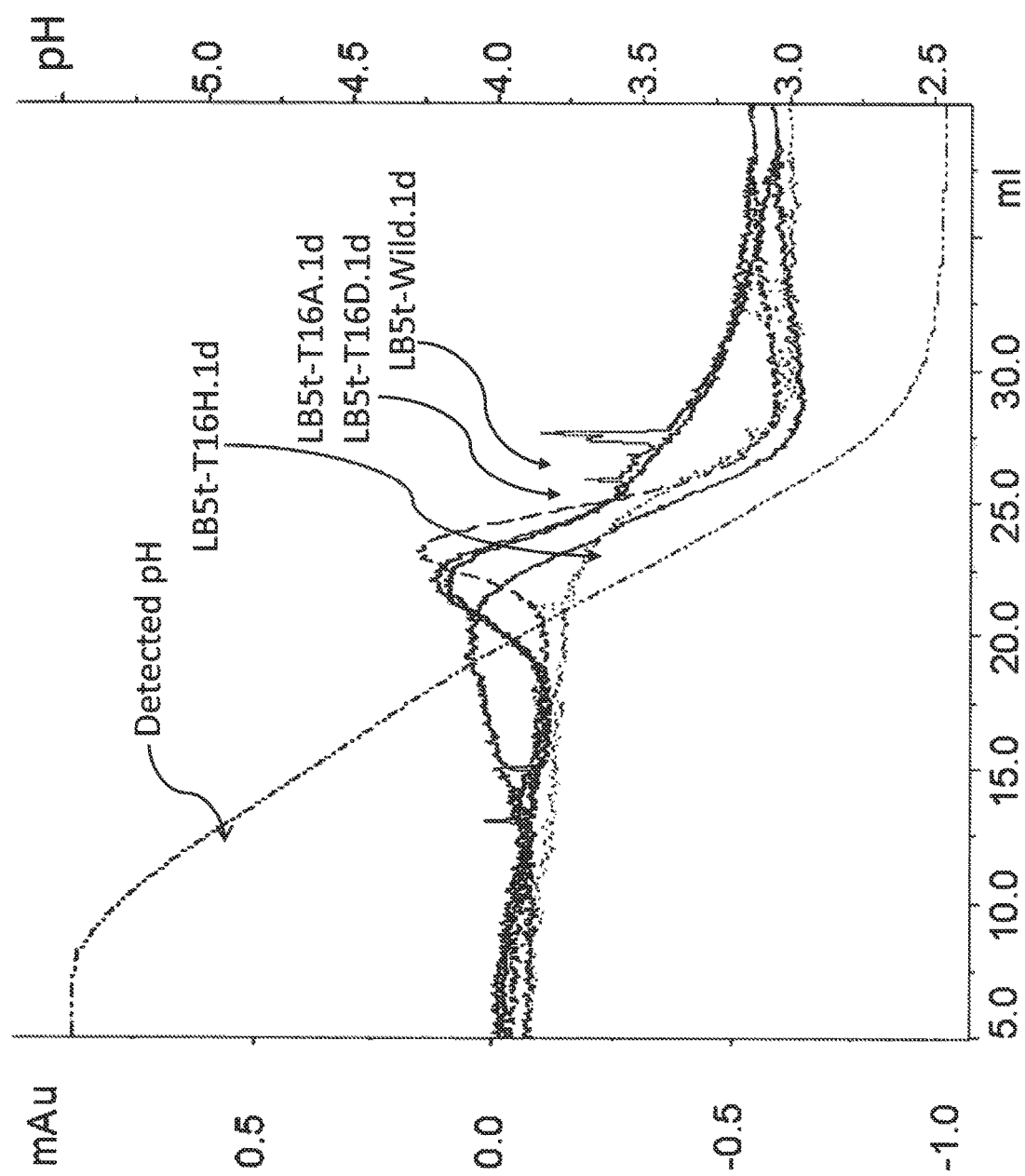
FIG. 3 are charts of affinity purification chromatography when various LB5t mutants prepared by introducing a mutation at the $16^{th}$ position were contacted with a carrier on which aRSV-Fab was immobilized and were eluted by pH gradient.

By affinity purification chromatography using aRSV-Fab-immobilized column prepared in Example 3(1), an acid dissociation pH at which each mutant LB5t prepared in Example 1 (2) was eluted and which corresponded to the peak top of an elution curve of the mutant LB5t was measured. Specifically, AKTAprime plus system was used as a chromatography system. The column was equilibrated using ion exchange buffer A (50 mM citric acid—citrate Na, pH5.5). Into the column, 0.1 mL of a protein solution containing each mutant LB5t in the concentration of about 0.1 mg/mL was added, and the protein was eluted with the pH linear gradient from pH5.5 to pH2.5. More specifically, the ion exchange buffer A and ion exchange buffer B (50 mM CH$_3$COOH—CH$_3$COONa, 1 M NaCl, pH2.5) were used. While 20 column volume of the buffer was flown through the column, the concentration of the buffer B was linearly increased from 0% to 100% to identify an acid dissociation pH on the basis of an elution position. For example, chromatography charts of various mutants of which mutations were introduced at the 16$^{th}$ position are shown as FIG. 3 so that the charts can be compared with that of wild LB5t of Comparative example 3. In the experiment, various LB5t mutants according to one or more embodiments of the present invention, specifically LB5t-T16A.1d, LB5t-T16D.1d and LB5t-T16H.1d, were eluted earlier than LB5t-Wild.1d without mutation. The result demonstrates that the various LB5t mutants can be eluted at the pH closer to neutrality. In other words, the data demonstrated that the pH to dissociate the peptide according to one or more embodiments of the present invention from a VL-κ chain variable region-containing protein becomes closer to neutrality. The pH value which was specified in the experiment as the value corresponding to each elution peak top is shown in Table 3 in addition to the result of Comparative example 3.

TABLE 3

|  | Dissociation pH |
| --- | --- |
| LB5t-Wild.1d | 3.35 |
| LB5t-Q15H.1d | 3.90 |
| LB5t-T16A.1d | 3.60 |
| LB5t-T16D.1d | 3.60 |
| LB5t-T16H.1d | 3.90 |
| LB5t-A17H.1d | 3.90 |
| LB5t-T18D.1d | 3.85 |
| LB5t-T18H.1d | 3.90 |
| LB5t-T18Q.1d | 3.65 |

As the result shown in Table 3, the pH to dissociate each mutant from a VL-κ chain variable region-containing peptide became closer to neutrality.

Comparative Example 1: Preparation of Wild B5 Domain of PpL (LB5t-Wild.1d)

A transformant was prepared using the expression vector of LB5t-Wild.1d prepared in Example 1 similarly to the procedure of Example 1, and a protein solution was prepared by way of cultivation and purification.

Comparative Example 2: Evaluation of Affinity of LB5t-Wild.1d for aRSV-Fab

An affinity of LB5t-Wild.1d prepared in Comparative example 1 for RSV-Fab prepared in Example 2 (1) was evaluated similarly to the procedure of Example 2 (2). The result is shown in the above Table 2.

Comparative Example 3: Measurement of Acid Dissociation pH Between aRSV-Fab and LB5t-Wild.1d An acid dissociation pH of LB5t-Wild.1d prepared in Comparative example 1 was measured using RSV-Fab-immobilized carrier prepared in Example 3(1) similarly to the procedure of Example 3 (2). The result is shown in the above Table 3.

Example 4: Preparation of 4 Domains of Mutant PpL312 B5 Domain (LB5t-T16H.4d)

The amino acid sequence of SEQ ID NO: 51 (LB5t-T16H.4d) was designed. The amino acid sequence corresponded to 4 amino acid sequences of mutant B5 domains of SEQ ID NO: 46 connected each other through the amino acid sequence between VL-κ-binding domains contained PpL312 of SEQ ID NO: 1. A base sequence of SEQ ID NO: 52 encoding the peptide was designed by reverse translation from the amino acid sequence of SEQ ID NO: 51. The artificially-synthesized DNA of SEQ ID NO: 53 was synthesized by outsourcing to Eurofins Genomics K.K. The DNA corresponded to the DNA of SEQ ID NO: 52 with PstI recognition site at the 5'-terminal and XbaI recognition site at the 3'-terminal. The expression plasmid after the subcloning was digested by restriction enzymes PstI and XbaI (Takara Bio Inc.). The obtained DNA fragment was ligated to Brevibacillus Expression vector pNCMO2 (Takara Bio Inc.) digested by the same restriction enzymes to prepare an expression vector corresponding to the Brevibacillus Expression vector pNCMO2 into which the DNA encoding the amino acid sequence of LB5t-T36H.4d was inserted. The ligation reaction was performed using Ligation high (manufactured by TOYOBO CO., LTD.) in accordance with the protocol attached to the product, and Escherichia coli JM109 (Takara Bio Inc.) was used for preparing the plasmid. The DNA base sequence of each expression vector was confirmed using DNA sequencer 3130x1 Genetic Analyzer (Applied Biosystems). A PCR sequencing method of each plasmid DNA was conducted using BigDye Terminator v.1.1 Cycle Sequencing Kit (Applied Biosystems) in accordance with the attached protocol, and the obtained sequencing product was purified using a plasmid purification kit ("Big-Dye XTerminator Purification Kit" manufactured by Applied Biosystems) in accordance with the attached protocol to be used for sequence analysis.

Brevibacillus choshinensis SP3 (Takara Bio Inc.) was transformed using the obtained plasmid, and the obtained transformant which could produce and secrete LB5t-T16H.4d was cultivated. Specifically, the transformant was cultivated with shaking in 30 mL of culture medium A (polypeptone 3.0%, yeast extract 0.5%, glucose 3%, magnesium sulfate 0.01%, ferric sulfate 0.001%, manganese chloride 0.001%, zinc chloride 0.0001%) containing 60 μg/mL of neomycin at 30° C. for 3 days. After the cultivation, the culture medium was centrifuge at 15,000 rpm and at 25° C. for 5 minutes to separate the bacterial body.

From the obtained culture supernatant, LB5t-T16H.4d was purified by cation exchange chromatography using UnoSphere S (Bio-Rad). UnoSphere S was packed into Tricorn 10/200 (GE Healthcare Bioscience). Specifically, sodium acetate was added to the culture supernatant so that the final concentration became 50 mM, and the pH was adjusted to 4.0 using acetic acid. UnoSphere S column was equilibrated using a cation exchange buffer A (50 mM $CH_3COOH$—$CH_3COONa$, pH4.0). The culture supernatant was added to the column, and the column was washed using the cation exchange buffer A. Then, the cation exchange buffer A and a cation exchange buffer B (50 mM $CH_3COOH$—$CH_3COONa$, 1 M NaCl, pH4.0) were flown with concentration gradient of a salt, and LB5t-T16H.4d was collected during the elution. Next, LB5t-T16H.4d was purified by anion exchange chromatography using Nuvia Q column (Bio-Rad). Nuvia Q was packed into Tricorn 10/200 (GE Healthcare Bioscience). Specifically, the collected LB5t-T16H.4d solution was subjected to dialysis using an anion exchange buffer A (50 mM Tris-HCl, pH8.0). Nuvia Q column was equilibrated using the anion exchange buffer A. The collected LB5t-T16H.4d solution was added to the equilibrated Nuvia Q column, and the column was washed using the anion exchange buffer A. Then, the anion exchange buffer A and an anion exchange buffer B (50 mM Tris-HCl, 1.0 M NaCl, pH8.0) were flown with concentration gradient of a salt, and LB5t-T16H.4d was collected during the elution. The collected LB5t-T16H.4d was subjected to dialysis again using ultrapure water, and an aqueous solution containing LB5t-T16H.4d only was obtained as the final purified sample. The purification of protein by chromatography using the above-described column was conducted using AKTAavant 25 system (GE Healthcare Bioscience).

Example 5: Preparation of Carrier on which 4 Domains of Mutant PpL312 B5 Domain were Immobilized The LB5t-T16H.4d prepared in Example 4 was immobilized on a water-insoluble cellulose carrier. As a water-insoluble cellulose carrier, highly crosslinked crystalline cellulose (manufactured by JNC Corporation, corresponding to a gel prepared by the method described in JP 2009-242770 A or US 20090062118 A) was used. For the immobilization, an epoxy method was used as the immobilization method.

Specifically, 2 mL-gel of the carrier was washed using 10 mL of ultrapure water three times on a glass filter. Then, the washed carrier was added into a centrifuge tube, and the predetermined amount of 1,4-bis(2,3-epoxypropoxy)butane was added thereto. The mixture was stirred at 37° C. for 30 minutes. After 30 minutes, 9.2 M sodium hydroxide aqueous solution was added so that the final concentration became 1 M. The mixture was stirred at 37° C. for 2 hours. The carrier was added on a glass filter, and the reaction solution was removed by reduced pressure. The carrier was washed using 30 mL of ultrapure water on the glass filter to obtain epoxidized carrier.

Then, LB5t-T16H.4d was immobilized on the epoxidized carrier. Specifically, 1.5 mL of the epoxidized carrier was added into a centrifuge tube, and LB5t-T16H.4d solution was further added thereto for a reaction at 37° C. for 30 minutes. After the reaction, sodium sulfate powder was added thereto so that the final concentration became 0.6 M. After adding sodium sulfate, a reaction was conducted at 37° C. for 2 hours. After the reaction, the carrier was added on a glass filter, and washed using 5 mL of a immobilization buffer (150 mM $Na_2HPO_4$, 1 mM EDTA, pH8.5) three times to recover unreacted LB5t-T16H.4d. Then, the carrier was washed using 5 mL of ultrapure water three times and 5 mL of an inactivation buffer containing thioglycerol (200 mM $NaHCO_3$, 100 mM NaCl, 1 mM EDTA, pH8.0) three times. The carrier was dispersed in the inactivation buffer containing thioglycerol and recovered, and added into a centrifuge tube to conduct reaction overnight. Next, the carrier was added on a glass filter, and washed using ultrapure water and 5 mL of a washing buffer (100 mM Tris-HCl, 150 mM NaCl, pH8.0) three times. The carrier was added into a centrifuge tube and stirred at 25° C. for 20 minutes. The carrier was added on a glass filter and washed using 5 mL of ultrapure water three times. The carrier was further washed using 10 mL of ultrapure water and 10 mL of 20% ethanol. Then, the carrier was dispersed in 20% ethanol and recovered to obtain LB5t-T16H.4d-immobilized carrier.

The absorbance of the recovered unreacted LB5t-T16H.4d at 280 nm was measured using a spectrometer. An amount of unreacted LB5t-T36H.4d was calculated from the measured absorbance and the absorption coefficient calculated from the amino acid sequence. An amount of the immobilized LB5t-T16H.4d was calculated from the difference of the amount of the used LB5t-T16H.4d and the calculated amount of the unreacted LB5t-T36H.4d, and the ligand density was further calculated from the volume of the carrier. The ligand density of the prepared carrier is shown in Table 4.

TABLE 4

| Carrier | Ligand density (mg/mL/gel) |
| --- | --- |
| Example 5 | 2.9 |

Example 6: Chromatography Experiment Using Carrier on which 4 Mutant PpL312 B5 Domains were Immobilized In Tricorn 5/50 column (GE Healthcare Bioscience), 1 mL-gel of the carrier prepared in Example 5 was packed. The column was connected to chromatography system AKTAavant 25 to measure the acid dissociation pH corresponding to the elution peak top of aRSV-Fab prepared in Example 2(1). Specifically, the column was equilibrated using an ion exchange buffer A (50 mM citric acid—citrate Na, pH5.0), and 1.0 mL of 1.0 mg/mL aRSV-Fab solution was added to the column. The Fab was eluted with the pH linear gradient from pH5.0 to pH2.4. More specifically, the ion exchange buffer A and ion exchange buffer B (50 mM citric acid—citrate Na, pH2.4) were used. While 20 column volume of the buffer was flown through the column, the concentration of the buffer B was linearly increased from 0% to 100% to identify an acid dissociation pH from an elution position. The result is shown in Table 5.

TABLE 5

| Carrier | Elution pH |
| --- | --- |
| Example 5 | 3.66 |

As the result shown in Table 5, monoclonal Fab can be dissociated from the affinity separation matrix on which peptide according to one or more embodiments of the present invention prepared by connecting mutant B5 domains was immobilized at the pH relatively closer to neutrality.

Example 7: Additional Preparation of Various Mutant VL-κ Chain-Binding Domains and Evaluation of Acid Dissociation pH to Dissociate VL-κ Chain Variable Region-Containing Fab (1) Preparation of Expression Plasmid, and Synthesis and Purification of Protein Expression plasmids of mutants of LB5t-Wild.1d (SEQ ID NO: 16), LB1t-Wild.1d (SEQ ID NO: 12) and LC4t-Wild.1d (SEQ ID NO: 20) were additionally prepared. The expression plasmids for introducing a mutation, which plasmids had encoding DNA of LB1t-Wild.1d or LC4t-Wild.1d, were prepared using single strand oligo DNAs of SEQ ID Nos: 54 to 60 shown in Table 6 similarly to the method described in Example 1(1). It was confirmed by a base sequence analysis similarly to the method described in Example 1(1) that the DNA encoding LB1t-Wild.1d had the base sequence of SEQ ID NO: 62 and the DNA encoding LC4t-Wild.1d had the base sequence of SEQ ID NO: 63 in the prepared expression plasmids.

TABLE 6

| | single-strand oligo DNA | | | | Encoding | Amino |
|---|---|---|---|---|---|---|
| Wild type | f1-1 | f1-2 | f2-1 | f2-2 | DNA | acid |
| LB5t-Wild.1d | 23 | 24 | 25 | 26 | 22 | 16 |
| LB1t-Wild.1d | 54 | 55 | 56 | 57 | 62 | 12 |
| LC4t-Wild.1d | 58 | 59 | 60 | 61 | 63 | 20 |

The numbers in the table represent SEQ ID NOs.

The expression plasmids of various single domain type VL-κ chain-binding domain mutants were prepared by synthesizing the double strand DNA corresponding to f1 in FIG. 2 by PCR using each corresponding wild expression plasmid as a template and using DNA primer for 5'-side sequencing of plasmid vector pGEX-6P-1 and each of 3'-side DNA primer of SEQ ID NOs: 64 to 69 similarly to the procedure described in Example 1(1). The base sequence of an oligo DNA, the base sequence of cDNA encoding the mutant and the SEQ ID NO of the amino acid sequence of the mutant which were used for preparing each mutant are shown in Table 7. With respect to the each mutant, a transformant was prepared, and a protein solution was prepared through cultivation and purification similarly to Example 1.

TABLE 7

| Mutant | Primer DNA | Encoding DNA | Amino acid |
|---|---|---|---|
| LB5t-T16I.1d | 64 | 70 | 76 |
| LB5t-T16L.1d | 65 | 71 | 77 |
| LB5t-T16G.1d | 66 | 72 | 78 |
| LB1t-E18D.1d | 67 | 73 | 79 |
| LC4t-T16D.1d | 68 | 74 | 80 |
| LC4t-E18H.1d | 69 | 75 | 81 |

The numbers in the table represent SEQ ID NOs.

(2) Evaluation of Acid Dissociation pH Between Fab and Various Mutant VL-κ Chain-Binding Domains An acid dissociation pH between Fab and various mutant VL-κ chain-binding domains prepared in the above (1) was measured by using an aRSV-Fab-immobilized carrier or an aIgE-Fab-immobilized carrier. The aIgE-Fab was prepared from anti-IgE monoclonal IgG product (general name: “omalizumab”, product name: “xolair”, Novartis Pharma K.K.) by the procedure described in Example 2(1), and aRSV-Fab-immobilized carrier was prepared by immobilizing the Fab on a commercially-available prepacked column by the procedure described in Example 3(1). The acid dissociation pH between various mutant VL-κ chain-binding domains and aRSV-Fab or aIgE-Fab was measured by a similar chromatography experiment described in Example 3(2).

First, the evaluation result using an aRSV-Fab-immobilized carrier, in other words, the pH value corresponding to the peak top of each elution position, is shown in Table 8 in addition to the results of Comparative examples 3 and 5.

TABLE 8

| | Dissociation pH |
|---|---|
| LB5t-Wild.1d | 3.35 |
| LB5t-T16I.1d | 3.55 |
| LB5t-T16L.1d | 3.65 |
| LB1t-Wild.1d | 2.70 |
| LB1t-E18D.1d | 2.95 |

It was confirmed that the additional LB5t mutants of LB5t-T16I.1d and LB5t-T16L.1d were also eluted at the pH closer to neutrality in comparison with LB5t-Wild.1d without mutation. The result suggests that when the kind of an amino acid for mutation is a hydrophobic amino acid, a similar effect can be obtained. When the data is considered with the result of Example 3, it is meaningful to introduce the mutation of amino acid substitution at the 15$^{th}$ to 18$^{th}$ positions of SEQ ID NO: 21 by one or more embodiments of the present invention. In addition, with respect to a LB1t mutant, it was confirmed that the mutant of LB1t-E18D.1d into which the mutation of one or more embodiments of the present invention was introduced was eluted at the pH closer to neutrality in comparison with LB1t-Wild.1d into which the mutation was not introduced. The sequence identity between LB5t-Wild.1d (SEQ ID NO: 16) and LB1t-Wild.1d (SEQ ID NO: 12) is 62.3%. Thus, the above data suggests that even when a sequence identity is about 60% before introducing the mutation, one or more embodiments of the present invention can be applied to the peptide which has a function as a VL-κ chain-binding domain.

Next, the evaluation result using an aIgE-Fab-immobilized carrier is shown in Table 9 in addition to the results of Comparative examples 3 and 5.

TABLE 9

|  | Dissociation pH |
| --- | --- |
| LB5t-Wild.1d | 3.05 |
| LB5t-T16I.1d | 3.20 |
| LB5t-T16G.1d | 3.20 |
| LC4t-Wild.1d | 3.20 |
| LC4t-T16D.1d | 3.40 |
| LC4t-E18H.1d | 3.40 |

It was confirmed that the peptide according to one or more embodiments of the present invention was eluted at the pH closer to neutrality against a different kind of VL-κ chain variable region-containing protein in comparison with the peptide into which the mutation was not introduced as the above-described experimental result. The data suggests that the effect by the mutation according to one or more embodiments of the present invention is not restricted to a VL-κ chain variable region-containing protein having a specific sequence. In addition, the data suggests that the mutation according to one or more embodiments of the present invention can be applied to not only the Protein L derived from a specific strain but also a general Protein L or other protein which is considered to be an analog thereof, since the mutation prepared from C4 domain as a base showed a similar tendency.

Comparative Example 4: Preparation of Wild B1 Domain (LB1t-Wild.1d) and Wild C4 Domain (LC4t-Wild.1d) of PpL A transformant was prepared using the expression plasmid of LB1t-Wild.1d and LC4t-Wild.1d prepared in Example 7(1) similarly to the procedure of Example 7, and a protein solution was prepared by way of cultivation and purification.

Comparative Example 5: Evaluation of Acid Dissociation pH Between LB1t-Wild.1d and aRSV-Fab, and Evaluation of Acid Dissociation pH Between LC4t-Wild.1d and aIgE-Fab With respect to LB1t-Wild.1d prepared in Comparative example 4, an acid dissociation pH was measured using an aRSV-Fab-immobilized carrier prepared in Example 3(1) similarly to the procedure of Example 7(2). In addition, with respect to LC4t-Wild.1d prepared in Comparative example 4, an acid dissociation pH was measured using an aIgE-Fab-immobilized carrier prepared in Example 7(2) by a similar chromatography experiment described in Example 7(2). The analysis results are shown in the above-described Table 8 and Table 9.

Although embodiments of the disclosure have been described using specific terms, devices, and methods, such description is for illustrative purposes only. The words used are words of description rather than limitation. It is to be understood that changes and variations may be made by those of ordinary skill in the art without departing from the spirit or the scope of the present disclosure, which is set forth in the following claims. In addition, it should be understood that aspects of the various embodiments may be interchanged in whole or in part. Therefore, the spirit and scope of the appended claims should not be limited to the description of the preferred versions contained therein.

What is claimed is:

1. An immunoglobulin κ chain variable region-binding peptide, selected from the group consisting of:
 a first immunoglobulin κ chain variable region-binding peptide comprising an amino acid sequence selected from the group consisting of SEQ ID NOs: 12 to 20 with substitution of one or more amino acid residues at positions selected from the 15$^{th}$ position, the 16$^{th}$ position, the 17$^{th}$ position and the 18$^{th}$ position,
 wherein the 15$^{th}$ position is substituted by His, the 16$^{th}$ position is substituted by Ala, Asp, Gly, Ile, Leu or His, the 17$^{th}$ position is substituted by Glu or His, and/or the 18$^{th}$ position is substituted by Asp, Gln or His, and wherein an acid dissociation pH thereof is shifted to a neutral side relative to an acid dissociation pH of an immunoglobulin κ chain variable region-binding peptide comprising the amino acid sequence selected from the group consisting of SEQ ID NOs: 12 to 20 without the substitution;

a second immunoglobulin κ chain variable region-binding peptide comprising the amino acid sequence of the first immunoglobulin κ chain variable region-binding peptide, further comprising deletion, substitution and/or addition of 1-7 amino acid residues at positions other than the 15$^{th}$ position, the 16$^{th}$ position, the 17$^{th}$ position and the 18$^{th}$ position, wherein an acid dissociation pH thereof is shifted to a neutral side relative to the acid dissociation pH of the first immunoglobulin κ chain variable region-binding peptide; and a third immunoglobulin κ chain variable region-binding peptide comprising an amino acid sequence with a sequence identity of 90% or more to the amino acid sequence of the first immunoglobulin κ chain variable region-binding peptide, wherein an acid dissociation pH thereof is shifted to a neutral side relative to the acid dissociation pH of the first immunoglobulin κ chain variable region-binding peptide, provided that the one or more amino acid residues substituted at the positions selected from the 15$^{th}$ position, the 16$^{th}$ position, the 17$^{th}$ position and the 18$^{th}$ position are not further mutated.

2. The immunoglobulin κ chain variable region-binding peptide according to claim 1, wherein the 16$^{th}$ position in the amino acid sequence of the first immunoglobulin κ chain variable region-binding peptide is substituted by Ala, Asp, Gly, Ile, Leu or His, and/or the 18$^{th}$ position in the amino acid sequence of the first immunoglobulin κ chain variable region-binding peptide is substituted by Asp, Gln or His.

3. The immunoglobulin κ chain variable region-binding peptide according to claim 1, wherein the 15$^{th}$ position is substituted by His, the 16$^{th}$ position is substituted by Ala, Asp or His, the 17$^{th}$ position is substituted by His, and/or the 18$^{th}$ position is substituted by Asp, Gln or His in the amino acid sequence of the first immunoglobulin κ chain variable region-binding peptide.

4. The immunoglobulin κ chain variable region-binding peptide according to claim 1, wherein a position of the deletion, substitution and/or addition of the amino acid residue is N-terminal and/or C-terminal in the amino acid sequence of the second immunoglobulin κ chain variable region-binding peptide.

5. The immunoglobulin κ chain variable region-binding peptide according to claim 1, wherein the sequence identity is 95% or more in the amino acid sequence of the third immunoglobulin κ chain variable region-binding peptide.

6. An immunoglobulin κ chain variable region-binding peptide multimer, comprising two or more domains formed by connecting two or more of the immunoglobulin κ chain variable region-binding peptides according to claim 1.

7. An affinity separation matrix, wherein the immunoglobulin κ chain variable region-binding peptide multimer according to claim 6 is immobilized on a water-insoluble carrier as a ligand.

8. An affinity separation matrix, wherein the immunoglobulin κ chain variable region-binding peptide according to claim 1 is immobilized on a water-insoluble carrier as a ligand.

9. A method for producing a protein comprising an immunoglobulin κ chain variable region, the method comprising:

contacting the affinity separation matrix according to claim 8 with a liquid sample comprising the protein comprising the immunoglobulin κ chain variable region; and separating the protein bound on the affinity separation matrix from the affinity separation matrix.

10. An immunoglobulin κ chain variable region-binding peptide, comprising an amino acid sequence selected from the group consisting of SEQ ID NOs: 12 to 20 with substitution of one or more amino acid residues at positions selected from the 15$^{th}$ position, the 16$^{th}$ position, the 17$^{th}$ position and the 18$^{th}$ position, wherein the 15$^{th}$ position is substituted by His, the 16$^{th}$ position is substituted by Ala, Asp, Gly, Ile, Leu or His, the 17$^{th}$ position is substituted by Glu or His, and/or the 18$^{th}$ position is substituted by Asp, Gln or His, and wherein an acid dissociation pH thereof is shifted to a neutral side relative to an acid dissociation pH of an immunoglobulin κ chain variable region-binding peptide comprising the amino acid sequence selected from the group consisting of SEQ ID NOs: 12 to 20 without the substitution.

11. The immunoglobulin κ chain variable region-binding peptide according to claim 10, wherein the 15$^{th}$ position is substituted by His, the 16$^{th}$ position is substituted by Ala, Asp or His, the 17$^{th}$ position is substituted by His, and/or the 18$^{th}$ position is substituted by Asp, Gln or His.

\* \* \* \* \*

SEQUENCE LISTING

```
<160> NUMBER OF SEQ ID NOS: 81

<210> SEQ ID NO 1
<211> LENGTH: 719
<212> TYPE: PRT
<213> ORGANISM: Peptostreptococcus magnus

<400> SEQUENCE: 1

Met Ala Ala Leu Ala Gly Ala Ile Val Val Thr Gly Gly Val Gly Ser
1               5                   10                  15

Tyr Ala Ala Asp Glu Pro Ile Asp Leu Glu Lys Leu Glu Glu Lys Arg
                20                  25                  30

Asp Lys Glu Asn Val Gly Asn Leu Pro Lys Phe Asp Asn Glu Val Lys
            35                  40                  45

Asp Gly Ser Glu Asn Pro Met Ala Lys Tyr Pro Asp Phe Asp Glu
        50                  55                  60

Ala Ser Thr Arg Phe Glu Thr Glu Asn Asn Glu Phe Glu Glu Lys Lys
65                  70                  75                  80
```

-continued

Val Val Ser Asp Asn Phe Phe Asp Gln Ser Glu His Pro Phe Val Glu
            85                  90                  95

Asn Lys Glu Glu Thr Pro Glu Thr Pro Glu Thr Asp Ser Glu Glu Glu
                100                 105                 110

Val Thr Ile Lys Ala Asn Leu Ile Phe Ala Asn Gly Ser Thr Gln Thr
        115                 120                 125

Ala Glu Phe Lys Gly Thr Phe Glu Lys Ala Thr Ser Glu Ala Tyr Ala
    130                 135                 140

Tyr Ala Asp Thr Leu Lys Lys Asp Asn Gly Glu Tyr Thr Val Asp Val
145                 150                 155                 160

Ala Asp Lys Gly Tyr Thr Leu Asn Ile Lys Phe Ala Gly Lys Glu Lys
                165                 170                 175

Thr Pro Glu Glu Pro Lys Glu Val Thr Ile Lys Ala Asn Leu Ile
                180                 185                 190

Tyr Ala Asp Gly Lys Thr Gln Thr Ala Glu Phe Lys Gly Thr Phe Glu
        195                 200                 205

Glu Ala Thr Ala Glu Ala Tyr Arg Tyr Ala Asp Ala Leu Lys Lys Asp
    210                 215                 220

Asn Gly Glu Tyr Thr Val Asp Val Ala Asp Lys Gly Tyr Thr Leu Asn
225                 230                 235                 240

Ile Lys Phe Ala Gly Lys Glu Lys Thr Pro Glu Glu Pro Lys Glu Glu
                245                 250                 255

Val Thr Ile Lys Ala Asn Leu Ile Tyr Ala Asp Gly Lys Thr Gln Thr
        260                 265                 270

Ala Glu Phe Lys Gly Thr Phe Glu Glu Ala Thr Ala Glu Ala Tyr Arg
    275                 280                 285

Tyr Ala Asp Leu Leu Ala Lys Glu Asn Gly Lys Tyr Thr Val Asp Val
    290                 295                 300

Ala Asp Lys Gly Tyr Thr Leu Asn Ile Lys Phe Ala Gly Lys Glu Lys
305                 310                 315                 320

Thr Pro Glu Glu Pro Lys Glu Val Thr Ile Lys Ala Asn Leu Ile
                325                 330                 335

Tyr Ala Asp Gly Lys Thr Gln Thr Ala Glu Phe Lys Gly Thr Phe Ala
        340                 345                 350

Glu Ala Thr Ala Glu Ala Tyr Arg Tyr Ala Asp Leu Leu Ala Lys Glu
    355                 360                 365

Asn Gly Lys Tyr Thr Ala Asp Leu Glu Asp Gly Gly Tyr Thr Ile Asn
370                 375                 380

Ile Arg Phe Ala Gly Lys Lys Val Asp Glu Lys Pro Glu Glu Lys Glu
385                 390                 395                 400

Gln Val Thr Ile Lys Glu Asn Ile Tyr Phe Glu Asp Gly Thr Val Gln
                405                 410                 415

Thr Ala Thr Phe Lys Gly Thr Phe Ala Glu Ala Thr Ala Glu Ala Tyr
            420                 425                 430

Arg Tyr Ala Asp Leu Leu Ser Lys Glu His Gly Lys Tyr Thr Ala Asp
        435                 440                 445

Leu Glu Asp Gly Gly Tyr Thr Ile Asn Ile Arg Phe Ala Gly Lys Glu
    450                 455                 460

Glu Pro Glu Glu Thr Pro Glu Lys Pro Glu Val Gln Asp Gly Tyr Ala
465                 470                 475                 480

Ser Tyr Glu Glu Ala Glu Ala Ala Lys Glu Ala Leu Lys Asn Asp
                485                 490                 495

```
Asp Val Asn Lys Ser Tyr Thr Ile Arg Gln Gly Ala Asp Gly Arg Tyr
            500                 505                 510

Tyr Tyr Val Leu Ser Pro Val Glu Ala Glu Glu Lys Pro Glu Ala
        515                 520                 525

Gln Asn Gly Tyr Ala Thr Tyr Glu Glu Ala Glu Ala Ala Lys Lys
        530                 535                 540

Ala Leu Glu Asn Asp Pro Ile Asn Lys Ser Tyr Ser Ile Arg Gln Gly
545                 550                 555                 560

Ala Asp Gly Arg Tyr Tyr Val Leu Ser Pro Val Glu Ala Glu Thr
        565                 570                 575

Pro Glu Lys Pro Val Glu Pro Ser Glu Pro Ser Thr Pro Asp Val Pro
        580                 585                 590

Ser Asn Pro Ser Asn Pro Ser Thr Pro Asp Val Pro Ser Thr Pro Asp
        595                 600                 605

Val Pro Ser Asn Pro Ser Thr Pro Glu Val Pro Ser Asn Pro Ser Thr
        610                 615                 620

Pro Gly Asn Glu Glu Lys Pro Gly Asn Glu Gln Lys Pro Gly Asn Glu
625                 630                 635                 640

Gln Lys Pro Gly Asn Glu Gln Lys Pro Gly Asn Glu Gln Lys Pro Gly
        645                 650                 655

Asn Glu Gln Lys Pro Asp Gln Pro Ser Lys Pro Glu Lys Glu Glu Asn
        660                 665                 670

Gly Lys Gly Gly Val Asp Ser Pro Lys Lys Glu Lys Ala Ala Leu
        675                 680                 685

Pro Lys Ala Gly Ser Glu Ala Glu Ile Leu Thr Leu Ala Ala Ser
        690                 695                 700

Leu Ser Ser Val Ala Gly Ala Phe Ile Ser Leu Lys Lys Arg Lys
705                 710                 715

<210> SEQ ID NO 2
<211> LENGTH: 992
<212> TYPE: PRT
<213> ORGANISM: Peptostreptococcus magnus

<400> SEQUENCE: 2

Met Lys Ile Asn Lys Lys Leu Leu Met Ala Ala Leu Ala Gly Ala Ile
1               5                   10                  15

Val Val Gly Gly Gly Ala Asn Ala Tyr Ala Ala Glu Glu Asp Asn Thr
            20                  25                  30

Asp Asn Asn Leu Ser Met Asp Glu Ile Ser Asp Ala Tyr Phe Asp Tyr
        35                  40                  45

His Gly Asp Val Ser Asp Ser Val Asp Pro Val Glu Glu Ile Asp
    50                  55                  60

Glu Ala Leu Ala Lys Ala Leu Ala Ala Lys Glu Thr Ala Lys Lys
65                  70                  75                  80

His Ile Asp Ser Leu Asn His Leu Ser Glu Thr Ala Lys Lys Leu Ala
            85                  90                  95

Lys Asn Asp Ile Asp Ser Ala Thr Thr Ile Asn Ala Ile Asn Asp Ile
            100                 105                 110

Val Ala Arg Ala Asp Val Met Glu Arg Lys Thr Ala Glu Lys Glu Glu
            115                 120                 125

Ala Glu Lys Leu Ala Ala Ala Lys Glu Thr Ala Lys Lys His Ile Asp
        130                 135                 140

Glu Leu Lys His Leu Ala Asp Lys Thr Lys Glu Leu Ala Lys Arg Asp
145                 150                 155                 160
```

```
Ile Asp Ser Ala Thr Thr Ile Asn Ala Ile Asn Asp Ile Val Ala Arg
                165                 170                 175

Ala Asp Val Met Glu Arg Lys Thr Ala Glu Lys Glu Ala Glu Lys
        180                 185                 190

Leu Ala Ala Ala Lys Glu Thr Ala Lys Lys His Ile Asp Glu Leu Lys
            195                 200                 205

His Leu Ala Asp Lys Thr Lys Glu Leu Ala Lys Arg Asp Ile Asp Ser
        210                 215                 220

Ala Thr Thr Ile Asp Ala Ile Asn Asp Ile Val Ala Arg Ala Asp Val
225                 230                 235                 240

Met Glu Arg Lys Leu Ser Glu Lys Glu Thr Pro Glu Pro Glu Glu Glu
                245                 250                 255

Val Thr Ile Lys Ala Asn Leu Ile Phe Ala Asp Gly Ser Thr Gln Asn
                260                 265                 270

Ala Glu Phe Lys Gly Thr Phe Ala Lys Ala Val Ser Asp Ala Tyr Ala
            275                 280                 285

Tyr Ala Asp Ala Leu Lys Lys Asp Asn Gly Glu Tyr Thr Val Asp Val
        290                 295                 300

Ala Asp Lys Gly Leu Thr Leu Asn Ile Lys Phe Ala Gly Lys Lys Glu
305                 310                 315                 320

Lys Pro Glu Glu Pro Lys Glu Glu Val Thr Ile Lys Val Asn Leu Ile
                325                 330                 335

Phe Ala Asp Gly Lys Thr Gln Thr Ala Glu Phe Lys Gly Thr Phe Glu
            340                 345                 350

Glu Ala Thr Ala Lys Ala Tyr Ala Tyr Ala Asp Leu Leu Ala Lys Glu
        355                 360                 365

Asn Gly Glu Tyr Thr Ala Asp Leu Glu Asp Gly Gly Asn Thr Ile Asn
        370                 375                 380

Ile Lys Phe Ala Gly Lys Glu Thr Pro Glu Thr Pro Glu Glu Pro Lys
385                 390                 395                 400

Glu Glu Val Thr Ile Lys Val Asn Leu Ile Phe Ala Asp Gly Lys Ile
                405                 410                 415

Gln Thr Ala Glu Phe Lys Gly Thr Phe Glu Glu Ala Thr Ala Lys Ala
            420                 425                 430

Tyr Ala Tyr Ala Asn Leu Leu Ala Lys Glu Asn Gly Glu Tyr Thr Ala
        435                 440                 445

Asp Leu Glu Asp Gly Gly Asn Thr Ile Asn Ile Lys Phe Ala Gly Lys
    450                 455                 460

Glu Thr Pro Glu Thr Pro Glu Glu Pro Lys Glu Glu Val Thr Ile Lys
465                 470                 475                 480

Val Asn Leu Ile Phe Ala Asp Gly Lys Thr Gln Thr Ala Glu Phe Lys
                485                 490                 495

Gly Thr Phe Glu Glu Ala Thr Ala Glu Ala Tyr Arg Tyr Ala Asp Leu
            500                 505                 510

Leu Ala Lys Val Asn Gly Glu Tyr Thr Ala Asp Leu Glu Asp Gly Gly
        515                 520                 525

Tyr Thr Ile Asn Ile Lys Phe Ala Gly Lys Glu Gln Pro Gly Glu Asn
        530                 535                 540

Pro Gly Ile Thr Ile Asp Glu Trp Leu Leu Lys Asn Ala Lys Glu Glu
545                 550                 555                 560

Ala Ile Lys Glu Leu Lys Glu Ala Gly Ile Thr Ser Asp Leu Tyr Phe
                565                 570                 575
```

```
Ser Leu Ile Asn Lys Ala Lys Thr Val Glu Gly Val Glu Ala Leu Lys
            580                 585                 590
Asn Glu Ile Leu Lys Ala His Ala Gly Glu Thr Pro Glu Leu Lys
        595                 600                 605
Asp Gly Tyr Ala Thr Tyr Glu Ala Glu Ala Ala Lys Glu Ala
    610                 615                 620
Leu Lys Asn Asp Asp Val Asn Asn Ala Tyr Glu Ile Val Gln Gly Ala
625                 630                 635                 640
Asp Gly Arg Tyr Tyr Tyr Val Leu Lys Ile Glu Val Ala Asp Glu Glu
                645                 650                 655
Glu Pro Gly Glu Asp Thr Pro Glu Val Gln Glu Gly Tyr Ala Thr Tyr
            660                 665                 670
Glu Glu Ala Glu Ala Ala Ala Lys Glu Ala Leu Lys Glu Asp Lys Val
        675                 680                 685
Asn Asn Ala Tyr Glu Val Val Gln Gly Ala Asp Gly Arg Tyr Tyr Tyr
    690                 695                 700
Val Leu Lys Ile Glu Asp Lys Glu Asp Glu Gln Pro Gly Glu Glu Pro
705                 710                 715                 720
Gly Glu Asn Pro Gly Ile Thr Ile Asp Glu Trp Leu Leu Lys Asn Ala
                725                 730                 735
Lys Glu Asp Ala Ile Lys Glu Leu Lys Glu Ala Gly Ile Ser Ser Asp
            740                 745                 750
Ile Tyr Phe Asp Ala Ile Asn Lys Ala Lys Thr Val Glu Gly Val Glu
        755                 760                 765
Ala Leu Lys Asn Glu Ile Leu Lys Ala His Ala Glu Lys Pro Gly Glu
    770                 775                 780
Asn Pro Gly Ile Thr Ile Asp Glu Trp Leu Leu Lys Asn Ala Lys Glu
785                 790                 795                 800
Ala Ala Ile Lys Glu Leu Lys Glu Ala Gly Ile Thr Ala Glu Tyr Leu
                805                 810                 815
Phe Asn Leu Ile Asn Lys Ala Lys Thr Val Glu Gly Val Glu Ser Leu
            820                 825                 830
Lys Asn Glu Ile Leu Lys Ala His Ala Glu Lys Pro Gly Glu Asn Pro
        835                 840                 845
Gly Ile Thr Ile Asp Glu Trp Leu Leu Lys Asn Ala Lys Glu Asp Ala
    850                 855                 860
Ile Lys Glu Leu Lys Glu Ala Gly Ile Thr Ser Asp Ile Tyr Phe Asp
865                 870                 875                 880
Ala Ile Asn Lys Ala Lys Thr Ile Glu Gly Val Glu Ala Leu Lys Asn
                885                 890                 895
Glu Ile Leu Lys Ala His Lys Lys Asp Glu Glu Pro Gly Lys Lys Pro
            900                 905                 910
Gly Glu Asp Lys Lys Pro Glu Asp Lys Lys Pro Gly Glu Asp Lys Lys
        915                 920                 925
Pro Glu Asp Lys Lys Pro Gly Glu Asp Lys Lys Pro Glu Asp Lys Lys
    930                 935                 940
Pro Gly Lys Thr Asp Lys Asp Ser Pro Asn Lys Lys Lys Ala Lys
945                 950                 955                 960
Leu Pro Lys Ala Gly Ser Glu Ala Glu Ile Leu Thr Leu Ala Ala Ala
                965                 970                 975
Ala Leu Ser Thr Ala Ala Gly Ala Tyr Val Ser Leu Lys Lys Arg Lys
            980                 985                 990
```

<210> SEQ ID NO 3
<211> LENGTH: 76
<212> TYPE: PRT
<213> ORGANISM: Peptostreptococcus magnus

<400> SEQUENCE: 3

Lys Glu Glu Thr Pro Glu Thr Pro Glu Thr Asp Ser Glu Glu Val
1               5                   10                  15

Thr Ile Lys Ala Asn Leu Ile Phe Ala Asn Gly Ser Thr Gln Thr Ala
            20                  25                  30

Glu Phe Lys Gly Thr Phe Glu Lys Ala Thr Ser Glu Ala Tyr Ala Tyr
        35                  40                  45

Ala Asp Thr Leu Lys Lys Asp Asn Gly Glu Tyr Thr Val Asp Val Ala
    50                  55                  60

Asp Lys Gly Tyr Thr Leu Asn Ile Lys Phe Ala Gly
65                  70                  75

<210> SEQ ID NO 4
<211> LENGTH: 72
<212> TYPE: PRT
<213> ORGANISM: Peptostreptococcus magnus

<400> SEQUENCE: 4

Lys Glu Lys Thr Pro Glu Glu Pro Lys Glu Glu Val Thr Ile Lys Ala
1               5                   10                  15

Asn Leu Ile Tyr Ala Asp Gly Lys Thr Gln Thr Ala Glu Phe Lys Gly
            20                  25                  30

Thr Phe Glu Glu Ala Thr Ala Glu Ala Tyr Arg Tyr Ala Asp Ala Leu
        35                  40                  45

Lys Lys Asp Asn Gly Glu Tyr Thr Val Asp Val Ala Asp Lys Gly Tyr
    50                  55                  60

Thr Leu Asn Ile Lys Phe Ala Gly
65                  70

<210> SEQ ID NO 5
<211> LENGTH: 72
<212> TYPE: PRT
<213> ORGANISM: Peptostreptococcus magnus

<400> SEQUENCE: 5

Lys Glu Lys Thr Pro Glu Glu Pro Lys Glu Glu Val Thr Ile Lys Ala
1               5                   10                  15

Asn Leu Ile Tyr Ala Asp Gly Lys Thr Gln Thr Ala Glu Phe Lys Gly
            20                  25                  30

Thr Phe Glu Glu Ala Thr Ala Glu Ala Tyr Arg Tyr Ala Asp Leu Leu
        35                  40                  45

Ala Lys Glu Asn Gly Lys Tyr Thr Val Asp Val Ala Asp Lys Gly Tyr
    50                  55                  60

Thr Leu Asn Ile Lys Phe Ala Gly
65                  70

<210> SEQ ID NO 6
<211> LENGTH: 72
<212> TYPE: PRT
<213> ORGANISM: Peptostreptococcus magnus

<400> SEQUENCE: 6

Lys Glu Lys Thr Pro Glu Glu Pro Lys Glu Glu Val Thr Ile Lys Ala
1               5                   10                  15

```
Asn Leu Ile Tyr Ala Asp Gly Lys Thr Gln Thr Ala Glu Phe Lys Gly
            20                  25                  30

Thr Phe Ala Glu Ala Thr Ala Glu Ala Tyr Arg Tyr Ala Asp Leu Leu
        35                  40                  45

Ala Lys Glu Asn Gly Lys Tyr Thr Ala Asp Leu Glu Asp Gly Gly Tyr
50                  55                  60

Thr Ile Asn Ile Arg Phe Ala Gly
65                  70
```

<210> SEQ ID NO 7
<211> LENGTH: 73
<212> TYPE: PRT
<213> ORGANISM: Peptostreptococcus magnus

<400> SEQUENCE: 7

```
Lys Lys Val Asp Glu Lys Pro Glu Glu Lys Gln Val Thr Ile Lys
1               5                   10                  15

Glu Asn Ile Tyr Phe Glu Asp Gly Thr Val Gln Thr Ala Thr Phe Lys
            20                  25                  30

Gly Thr Phe Ala Glu Ala Thr Ala Glu Ala Tyr Arg Tyr Ala Asp Leu
        35                  40                  45

Leu Ser Lys Glu His Gly Lys Tyr Thr Ala Asp Leu Glu Asp Gly Gly
50                  55                  60

Tyr Thr Ile Asn Ile Arg Phe Ala Gly
65                  70
```

<210> SEQ ID NO 8
<211> LENGTH: 71
<212> TYPE: PRT
<213> ORGANISM: Peptostreptococcus magnus

<400> SEQUENCE: 8

```
Lys Glu Thr Pro Glu Pro Glu Glu Val Thr Ile Lys Ala Asn Leu
1               5                   10                  15

Ile Phe Ala Asp Gly Ser Thr Gln Asn Ala Glu Phe Lys Gly Thr Phe
            20                  25                  30

Ala Lys Ala Val Ser Asp Ala Tyr Ala Tyr Ala Asp Ala Leu Lys Lys
        35                  40                  45

Asp Asn Gly Glu Tyr Thr Val Asp Val Ala Asp Lys Gly Leu Thr Leu
50                  55                  60

Asn Ile Lys Phe Ala Gly Lys
65                  70
```

<210> SEQ ID NO 9
<211> LENGTH: 71
<212> TYPE: PRT
<213> ORGANISM: Peptostreptococcus magnus

<400> SEQUENCE: 9

```
Lys Glu Lys Pro Glu Glu Pro Lys Glu Glu Val Thr Ile Lys Val Asn
1               5                   10                  15

Leu Ile Phe Ala Asp Gly Lys Thr Gln Thr Ala Glu Phe Lys Gly Thr
            20                  25                  30

Phe Glu Glu Ala Thr Ala Lys Ala Tyr Ala Tyr Ala Asp Leu Leu Ala
        35                  40                  45

Lys Glu Asn Gly Glu Tyr Thr Ala Asp Leu Glu Asp Gly Gly Asn Thr
50                  55                  60

Ile Asn Ile Lys Phe Ala Gly
```

<210> SEQ ID NO 10
<211> LENGTH: 74
<212> TYPE: PRT
<213> ORGANISM: Peptostreptococcus magnus

<400> SEQUENCE: 10

Lys Glu Thr Pro Glu Thr Pro Glu Glu Pro Lys Glu Glu Val Thr Ile
1               5                   10                  15

Lys Val Asn Leu Ile Phe Ala Asp Gly Lys Ile Gln Thr Ala Glu Phe
            20                  25                  30

Lys Gly Thr Phe Glu Glu Ala Thr Ala Lys Ala Tyr Ala Tyr Ala Asn
        35                  40                  45

Leu Leu Ala Lys Glu Asn Gly Glu Tyr Thr Ala Asp Leu Glu Asp Gly
    50                  55                  60

Gly Asn Thr Ile Asn Ile Lys Phe Ala Gly
65                  70

<210> SEQ ID NO 11
<211> LENGTH: 75
<212> TYPE: PRT
<213> ORGANISM: Peptostreptococcus magnus

<400> SEQUENCE: 11

Lys Glu Thr Pro Glu Thr Pro Glu Glu Pro Lys Glu Glu Val Thr Ile
1               5                   10                  15

Lys Val Asn Leu Ile Phe Ala Asp Gly Lys Thr Gln Thr Ala Glu Phe
            20                  25                  30

Lys Gly Thr Phe Glu Glu Ala Thr Ala Glu Ala Tyr Arg Tyr Ala Asp
        35                  40                  45

Leu Leu Ala Lys Val Asn Gly Glu Tyr Thr Ala Asp Leu Glu Asp Gly
    50                  55                  60

Gly Tyr Thr Ile Asn Ile Lys Phe Ala Gly Lys
65                  70                  75

<210> SEQ ID NO 12
<211> LENGTH: 60
<212> TYPE: PRT
<213> ORGANISM: Peptostreptococcus magnus

<400> SEQUENCE: 12

Val Thr Ile Lys Ala Asn Leu Ile Phe Ala Asn Gly Ser Thr Gln Thr
1               5                   10                  15

Ala Glu Phe Lys Gly Thr Phe Glu Lys Ala Thr Ser Glu Ala Tyr Ala
            20                  25                  30

Tyr Ala Asp Thr Leu Lys Lys Asp Asn Gly Glu Tyr Thr Val Asp Val
        35                  40                  45

Ala Asp Lys Gly Tyr Thr Leu Asn Ile Lys Phe Ala
    50                  55                  60

<210> SEQ ID NO 13
<211> LENGTH: 60
<212> TYPE: PRT
<213> ORGANISM: Peptostreptococcus magnus

<400> SEQUENCE: 13

Val Thr Ile Lys Ala Asn Leu Ile Tyr Ala Asp Gly Lys Thr Gln Thr
1               5                   10                  15

Ala Glu Phe Lys Gly Thr Phe Glu Glu Ala Thr Ala Glu Ala Tyr Arg
            20                  25                  30

Tyr Ala Asp Ala Leu Lys Lys Asp Asn Gly Tyr Thr Val Asp Val
        35                  40                  45

Ala Asp Lys Gly Tyr Thr Leu Asn Ile Lys Phe Ala
    50                  55                  60

<210> SEQ ID NO 14
<211> LENGTH: 60
<212> TYPE: PRT
<213> ORGANISM: Peptostreptococcus magnus

<400> SEQUENCE: 14

Val Thr Ile Lys Ala Asn Leu Ile Tyr Ala Asp Gly Lys Thr Gln Thr
1               5                   10                  15

Ala Glu Phe Lys Gly Thr Phe Glu Glu Ala Thr Ala Glu Ala Tyr Arg
            20                  25                  30

Tyr Ala Asp Leu Leu Ala Lys Glu Asn Gly Lys Tyr Thr Val Asp Val
        35                  40                  45

Ala Asp Lys Gly Tyr Thr Leu Asn Ile Lys Phe Ala
    50                  55                  60

<210> SEQ ID NO 15
<211> LENGTH: 60
<212> TYPE: PRT
<213> ORGANISM: Peptostreptococcus magnus

<400> SEQUENCE: 15

Val Thr Ile Lys Ala Asn Leu Ile Tyr Ala Asp Gly Lys Thr Gln Thr
1               5                   10                  15

Ala Glu Phe Lys Gly Thr Phe Ala Glu Ala Thr Ala Glu Ala Tyr Arg
            20                  25                  30

Tyr Ala Asp Leu Leu Ala Lys Glu Asn Gly Lys Tyr Thr Ala Asp Leu
        35                  40                  45

Glu Asp Gly Gly Tyr Thr Ile Asn Ile Arg Phe Ala
    50                  55                  60

<210> SEQ ID NO 16
<211> LENGTH: 60
<212> TYPE: PRT
<213> ORGANISM: Peptostreptococcus magnus

<400> SEQUENCE: 16

Val Thr Ile Lys Glu Asn Ile Tyr Phe Glu Asp Gly Val Gln Thr
1               5                   10                  15

Ala Thr Phe Lys Gly Thr Phe Ala Glu Ala Thr Ala Glu Ala Tyr Arg
            20                  25                  30

Tyr Ala Asp Leu Leu Ser Lys Glu His Gly Lys Tyr Thr Ala Asp Leu
        35                  40                  45

Glu Asp Gly Gly Tyr Thr Ile Asn Ile Arg Phe Ala
    50                  55                  60

<210> SEQ ID NO 17
<211> LENGTH: 60
<212> TYPE: PRT
<213> ORGANISM: Peptostreptococcus magnus

<400> SEQUENCE: 17

Val Thr Ile Lys Ala Asn Leu Ile Phe Ala Asp Gly Ser Thr Gln Asn
1               5                   10                  15

```
Ala Glu Phe Lys Gly Thr Phe Ala Lys Ala Val Ser Asp Ala Tyr Ala
            20                  25                  30

Tyr Ala Asp Ala Leu Lys Lys Asp Asn Gly Glu Tyr Thr Val Asp Val
            35                  40                  45

Ala Asp Lys Gly Leu Thr Leu Asn Ile Lys Phe Ala
        50                  55                  60

<210> SEQ ID NO 18
<211> LENGTH: 60
<212> TYPE: PRT
<213> ORGANISM: Peptostreptococcus magnus

<400> SEQUENCE: 18

Val Thr Ile Lys Val Asn Leu Ile Phe Ala Asp Gly Lys Thr Gln Thr
1               5                   10                  15

Ala Glu Phe Lys Gly Thr Phe Glu Glu Ala Thr Ala Lys Ala Tyr Ala
            20                  25                  30

Tyr Ala Asp Leu Leu Ala Lys Glu Asn Gly Glu Tyr Thr Ala Asp Leu
            35                  40                  45

Glu Asp Gly Gly Asn Thr Ile Asn Ile Lys Phe Ala
        50                  55                  60

<210> SEQ ID NO 19
<211> LENGTH: 60
<212> TYPE: PRT
<213> ORGANISM: Peptostreptococcus magnus

<400> SEQUENCE: 19

Val Thr Ile Lys Val Asn Leu Ile Phe Ala Asp Gly Lys Ile Gln Thr
1               5                   10                  15

Ala Glu Phe Lys Gly Thr Phe Glu Glu Ala Thr Ala Lys Ala Tyr Ala
            20                  25                  30

Tyr Ala Asn Leu Leu Ala Lys Glu Asn Gly Glu Tyr Thr Ala Asp Leu
            35                  40                  45

Glu Asp Gly Gly Asn Thr Ile Asn Ile Lys Phe Ala
        50                  55                  60

<210> SEQ ID NO 20
<211> LENGTH: 60
<212> TYPE: PRT
<213> ORGANISM: Peptostreptococcus magnus

<400> SEQUENCE: 20

Val Thr Ile Lys Val Asn Leu Ile Phe Ala Asp Gly Lys Thr Gln Thr
1               5                   10                  15

Ala Glu Phe Lys Gly Thr Phe Glu Glu Ala Thr Ala Glu Ala Tyr Arg
            20                  25                  30

Tyr Ala Asp Leu Leu Ala Lys Val Asn Gly Glu Tyr Thr Ala Asp Leu
            35                  40                  45

Glu Asp Gly Gly Tyr Thr Ile Asn Ile Lys Phe Ala
        50                  55                  60

<210> SEQ ID NO 21
<211> LENGTH: 60
<212> TYPE: PRT
<213> ORGANISM: Artificial Sequence
<220> FEATURE:
<223> OTHER INFORMATION: engineered PpL analogue
<220> FEATURE:
<221> NAME/KEY: misc_feature
```

<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(11)
<223> OTHER INFORMATION: Xaa can be any naturally occurring amino acid
<220> FEATURE:
<221> NAME/KEY: misc_feature
<222> LOCATION: (13)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (24)..(25)
<223> OTHER INFORMATION: Xaa can be any naturally occurring amino acid
<220> FEATURE:
<221> NAME/KEY: misc_feature
<222> LOCATION: (27)..(29)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (35)..(36)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (40)..(41)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (48)..(49)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid

<400> SEQUENCE: 21

```
Val Thr Ile Lys Xaa Asn Xaa Xaa Xaa Xaa Xaa Gly Xaa Xaa Gln Xaa
1               5                   10                  15

Ala Xaa Phe Lys Gly Thr Phe Xaa Xaa Ala Xaa Xaa Xaa Ala Tyr Xaa
            20                  25                  30
```

Tyr Ala Xaa Xaa Leu Xaa Lys Xaa Xaa Gly Xaa Tyr Thr Xaa Asp Xaa
              35                  40                  45

Xaa Asp Xaa Gly Xaa Thr Xaa Asn Ile Xaa Phe Ala
 50                  55                  60

<210> SEQ ID NO 22
<211> LENGTH: 192
<212> TYPE: DNA
<213> ORGANISM: Artificial Sequence
<220> FEATURE:
<223> OTHER INFORMATION: PpL cDNA

<400> SEQUENCE: 22
gaacaggtta ccattaaaga gaacatctac tttgaagatg gcacggtaca gactgccacg      60
ttcaaaggta cgtttgcgga agctactgca gaagcttacc gctatgcgga cctgctctcg    120
aaagagcatg gcaaatacac agcggatctt gaagatggag gttacacaat caatattcgc    180
ttcgccggct aa                                                         192

<210> SEQ ID NO 23
<211> LENGTH: 66
<212> TYPE: DNA
<213> ORGANISM: Artificial Sequence
<220> FEATURE:
<223> OTHER INFORMATION: oligo DNA

<400> SEQUENCE: 23
cgtggatccg aacaggttac cattaaagag aacatctact ttgaagatgg cacggtacag     60
actgcc                                                                66

<210> SEQ ID NO 24
<211> LENGTH: 54
<212> TYPE: DNA
<213> ORGANISM: Artificial Sequence
<220> FEATURE:
<223> OTHER INFORMATION: oligo DNA

<400> SEQUENCE: 24
gcggtaagct tctgcagtag cttccgcaaa cgtacctttg aacgtggcag tctg           54

<210> SEQ ID NO 25
<211> LENGTH: 63
<212> TYPE: DNA
<213> ORGANISM: Artificial Sequence
<220> FEATURE:
<223> OTHER INFORMATION: oligo DNA

<400> SEQUENCE: 25
gcagaagctt accgctatgc ggacctgctc tcgaaagagc atggcaaata cacagcggat     60
ctt                                                                   63

<210> SEQ ID NO 26
<211> LENGTH: 60
<212> TYPE: DNA
<213> ORGANISM: Artificial Sequence
<220> FEATURE:
<223> OTHER INFORMATION: oligo DNA

<400> SEQUENCE: 26
gatgaattct agccggcga agcgaatatt gattgtgtaa cctccatctt caagatccgc      60

<210> SEQ ID NO 27
<211> LENGTH: 61

<212> TYPE: DNA
<213> ORGANISM: Artificial Sequence
<220> FEATURE:
<223> OTHER INFORMATION: oligo DNA

<400> SEQUENCE: 27
ggtaagcttc tgcagtagct tccgcaaacg tacctttgaa cgtggcagtg tgtaccgtgc    60
c                                                                    61

<210> SEQ ID NO 28
<211> LENGTH: 59
<212> TYPE: DNA
<213> ORGANISM: Artificial Sequence
<220> FEATURE:
<223> OTHER INFORMATION: oligo DNA

<400> SEQUENCE: 28
ggtaagcttc tgcagtagct tccgcaaacg tacctttgaa cgtggcagcc tgtaccgtg     59

<210> SEQ ID NO 29
<211> LENGTH: 59
<212> TYPE: DNA
<213> ORGANISM: Artificial Sequence
<220> FEATURE:
<223> OTHER INFORMATION: oligo DNA

<400> SEQUENCE: 29
ggtaagcttc tgcagtagct tccgcaaacg tacctttgaa cgtggcatcc tgtaccgtg     59

<210> SEQ ID NO 30
<211> LENGTH: 59
<212> TYPE: DNA
<213> ORGANISM: Artificial Sequence
<220> FEATURE:
<223> OTHER INFORMATION: oligo DNA

<400> SEQUENCE: 30
ggtaagcttc tgcagtagct tccgcaaacg tacctttgaa cgtggcatgc tgtaccgtg     59

<210> SEQ ID NO 31
<211> LENGTH: 55
<212> TYPE: DNA
<213> ORGANISM: Artificial Sequence
<220> FEATURE:
<223> OTHER INFORMATION: oligo DNA

<400> SEQUENCE: 31
ggtaagcttc tgcagtagct tccgcaaacg tacctttgaa cgtgtgagtc tgtac         55

<210> SEQ ID NO 32
<211> LENGTH: 52
<212> TYPE: DNA
<213> ORGANISM: Artificial Sequence
<220> FEATURE:
<223> OTHER INFORMATION: oligo DNA

<400> SEQUENCE: 32
ggtaagcttc tgcagtagct tccgcaaacg tacctttgaa gtcggcagtc tg            52

<210> SEQ ID NO 33
<211> LENGTH: 52
<212> TYPE: DNA
<213> ORGANISM: Artificial Sequence
<220> FEATURE:
<223> OTHER INFORMATION: oligo DNA

```
<400> SEQUENCE: 33
ggtaagcttc tgcagtagct tccgcaaacg tacctttgaa gtgggcagtc tg    52

<210> SEQ ID NO 34
<211> LENGTH: 52
<212> TYPE: DNA
<213> ORGANISM: Artificial Sequence
<220> FEATURE:
<223> OTHER INFORMATION: oligo DNA

<400> SEQUENCE: 34
ggtaagcttc tgcagtagct tccgcaaacg tacctttgaa ctgggcagtc tg    52

<210> SEQ ID NO 35
<211> LENGTH: 192
<212> TYPE: DNA
<213> ORGANISM: Artificial Sequence
<220> FEATURE:
<223> OTHER INFORMATION: DNA code

<400> SEQUENCE: 35
gaacaggtta ccattaaaga gaacatctac tttgaagatg gcacggtaca cactgccacg    60
ttcaaaggta cgtttgcgga agctactgca gaagcttacc gctatgcgga cctgctctcg   120
aaagagcatg gcaaatacac agcggatctt gaagatggag gttacacaat caatattcgc   180
ttcgccggct aa                                                       192

<210> SEQ ID NO 36
<211> LENGTH: 192
<212> TYPE: DNA
<213> ORGANISM: Artificial Sequence
<220> FEATURE:
<223> OTHER INFORMATION: DNA code

<400> SEQUENCE: 36
gaacaggtta ccattaaaga gaacatctac tttgaagatg gcacggtaca ggctgccacg    60
ttcaaaggta cgtttgcgga agctactgca gaagcttacc gctatgcgga cctgctctcg   120
aaagagcatg gcaaatacac agcggatctt gaagatggag gttacacaat caatattcgc   180
ttcgccggct aa                                                       192

<210> SEQ ID NO 37
<211> LENGTH: 192
<212> TYPE: DNA
<213> ORGANISM: Artificial Sequence
<220> FEATURE:
<223> OTHER INFORMATION: DNA code

<400> SEQUENCE: 37
gaacaggtta ccattaaaga gaacatctac tttgaagatg gcacggtaca ggatgccacg    60
ttcaaaggta cgtttgcgga agctactgca gaagcttacc gctatgcgga cctgctctcg   120
aaagagcatg gcaaatacac agcggatctt gaagatggag gttacacaat caatattcgc   180
ttcgccggct aa                                                       192

<210> SEQ ID NO 38
<211> LENGTH: 192
<212> TYPE: DNA
<213> ORGANISM: Artificial Sequence
<220> FEATURE:
<223> OTHER INFORMATION: DNA code

<400> SEQUENCE: 38
```

```
gaacaggtta ccattaaaga gaacatctac tttgaagatg gcacggtaca gcatgccacg    60
ttcaaaggta cgtttgcgga agctactgca gaagcttacc gctatgcgga cctgctctcg   120
aaagagcatg gcaaatacac agcggatctt gaagatggag gttacacaat caatattcgc   180
ttcgccggct aa                                                        192

<210> SEQ ID NO 39
<211> LENGTH: 192
<212> TYPE: DNA
<213> ORGANISM: Artificial Sequence
<220> FEATURE:
<223> OTHER INFORMATION: DNA code

<400> SEQUENCE: 39
gaacaggtta ccattaaaga gaacatctac tttgaagatg gcacggtaca gactcacacg    60
ttcaaaggta cgtttgcgga agctactgca gaagcttacc gctatgcgga cctgctctcg   120
aaagagcatg gcaaatacac agcggatctt gaagatggag gttacacaat caatattcgc   180
ttcgccggct aa                                                        192

<210> SEQ ID NO 40
<211> LENGTH: 192
<212> TYPE: DNA
<213> ORGANISM: Artificial Sequence
<220> FEATURE:
<223> OTHER INFORMATION: DNA code

<400> SEQUENCE: 40
gaacaggtta ccattaaaga gaacatctac tttgaagatg gcacggtaca gactgccgac    60
ttcaaaggta cgtttgcgga agctactgca gaagcttacc gctatgcgga cctgctctcg   120
aaagagcatg gcaaatacac agcggatctt gaagatggag gttacacaat caatattcgc   180
ttcgccggct aa                                                        192

<210> SEQ ID NO 41
<211> LENGTH: 192
<212> TYPE: DNA
<213> ORGANISM: Artificial Sequence
<220> FEATURE:
<223> OTHER INFORMATION: DNA code

<400> SEQUENCE: 41
gaacaggtta ccattaaaga gaacatctac tttgaagatg gcacggtaca gactgcccac    60
ttcaaaggta cgtttgcgga agctactgca gaagcttacc gctatgcgga cctgctctcg   120
aaagagcatg gcaaatacac agcggatctt gaagatggag gttacacaat caatattcgc   180
ttcgccggct aa                                                        192

<210> SEQ ID NO 42
<211> LENGTH: 192
<212> TYPE: DNA
<213> ORGANISM: Artificial Sequence
<220> FEATURE:
<223> OTHER INFORMATION: DNA code

<400> SEQUENCE: 42
gaacaggtta ccattaaaga gaacatctac tttgaagatg gcacggtaca gactgcccag    60
ttcaaaggta cgtttgcgga agctactgca gaagcttacc gctatgcgga cctgctctcg   120
aaagagcatg gcaaatacac agcggatctt gaagatggag gttacacaat caatattcgc   180
```
ttcgccggct aa    192

<210> SEQ ID NO 43
<211> LENGTH: 60
<212> TYPE: PRT
<213> ORGANISM: Artificial Sequence
<220> FEATURE:
<223> OTHER INFORMATION: PpL mutant

<400> SEQUENCE: 43

Val Thr Ile Lys Glu Asn Ile Tyr Phe Glu Asp Gly Thr Val His Thr
1               5                   10                  15

Ala Thr Phe Lys Gly Thr Phe Ala Glu Ala Thr Ala Glu Ala Tyr Arg
            20                  25                  30

Tyr Ala Asp Leu Leu Ser Lys Glu His Gly Lys Tyr Thr Ala Asp Leu
        35                  40                  45

Glu Asp Gly Gly Tyr Thr Ile Asn Ile Arg Phe Ala
    50                  55                  60

<210> SEQ ID NO 44
<211> LENGTH: 60
<212> TYPE: PRT
<213> ORGANISM: Artificial Sequence
<220> FEATURE:
<223> OTHER INFORMATION: PpL mutant

<400> SEQUENCE: 44

Val Thr Ile Lys Glu Asn Ile Tyr Phe Glu Asp Gly Thr Val Gln Ala
1               5                   10                  15

Ala Thr Phe Lys Gly Thr Phe Ala Glu Ala Thr Ala Glu Ala Tyr Arg
            20                  25                  30

Tyr Ala Asp Leu Leu Ser Lys Glu His Gly Lys Tyr Thr Ala Asp Leu
        35                  40                  45

Glu Asp Gly Gly Tyr Thr Ile Asn Ile Arg Phe Ala
    50                  55                  60

<210> SEQ ID NO 45
<211> LENGTH: 60
<212> TYPE: PRT
<213> ORGANISM: Artificial Sequence
<220> FEATURE:
<223> OTHER INFORMATION: PpL mutant

<400> SEQUENCE: 45

Val Thr Ile Lys Glu Asn Ile Tyr Phe Glu Asp Gly Thr Val Gln Asp
1               5                   10                  15

Ala Thr Phe Lys Gly Thr Phe Ala Glu Ala Thr Ala Glu Ala Tyr Arg
            20                  25                  30

Tyr Ala Asp Leu Leu Ser Lys Glu His Gly Lys Tyr Thr Ala Asp Leu
        35                  40                  45

Glu Asp Gly Gly Tyr Thr Ile Asn Ile Arg Phe Ala
    50                  55                  60

<210> SEQ ID NO 46
<211> LENGTH: 60
<212> TYPE: PRT
<213> ORGANISM: Artificial Sequence
<220> FEATURE:
<223> OTHER INFORMATION: PpL Mutant

<400> SEQUENCE: 46

Val Thr Ile Lys Glu Asn Ile Tyr Phe Glu Asp Gly Thr Val Gln His

```
                1               5                  10                  15
Ala Thr Phe Lys Gly Thr Phe Ala Glu Ala Thr Ala Glu Ala Tyr Arg
                20                  25                  30

Tyr Ala Asp Leu Leu Ser Lys Glu His Gly Lys Tyr Thr Ala Asp Leu
        35                  40                  45

Glu Asp Gly Gly Tyr Thr Ile Asn Ile Arg Phe Ala
        50                  55                  60

<210> SEQ ID NO 47
<211> LENGTH: 60
<212> TYPE: PRT
<213> ORGANISM: Artificial Sequence
<220> FEATURE:
<223> OTHER INFORMATION: PpL mutant

<400> SEQUENCE: 47

Val Thr Ile Lys Glu Asn Ile Tyr Phe Glu Asp Gly Thr Val Gln Thr
1               5                  10                  15

His Thr Phe Lys Gly Thr Phe Ala Glu Ala Thr Ala Glu Ala Tyr Arg
                20                  25                  30

Tyr Ala Asp Leu Leu Ser Lys Glu His Gly Lys Tyr Thr Ala Asp Leu
        35                  40                  45

Glu Asp Gly Gly Tyr Thr Ile Asn Ile Arg Phe Ala
        50                  55                  60

<210> SEQ ID NO 48
<211> LENGTH: 60
<212> TYPE: PRT
<213> ORGANISM: Artificial Sequence
<220> FEATURE:
<223> OTHER INFORMATION: PpL mutant

<400> SEQUENCE: 48

Val Thr Ile Lys Glu Asn Ile Tyr Phe Glu Asp Gly Thr Val Gln Thr
1               5                  10                  15

Ala Asp Phe Lys Gly Thr Phe Ala Glu Ala Thr Ala Glu Ala Tyr Arg
                20                  25                  30

Tyr Ala Asp Leu Leu Ser Lys Glu His Gly Lys Tyr Thr Ala Asp Leu
        35                  40                  45

Glu Asp Gly Gly Tyr Thr Ile Asn Ile Arg Phe Ala
        50                  55                  60

<210> SEQ ID NO 49
<211> LENGTH: 60
<212> TYPE: PRT
<213> ORGANISM: Artificial Sequence
<220> FEATURE:
<223> OTHER INFORMATION: PpL mutant

<400> SEQUENCE: 49

Val Thr Ile Lys Glu Asn Ile Tyr Phe Glu Asp Gly Thr Val Gln Thr
1               5                  10                  15

Ala His Phe Lys Gly Thr Phe Ala Glu Ala Thr Ala Glu Ala Tyr Arg
                20                  25                  30

Tyr Ala Asp Leu Leu Ser Lys Glu His Gly Lys Tyr Thr Ala Asp Leu
        35                  40                  45

Glu Asp Gly Gly Tyr Thr Ile Asn Ile Arg Phe Ala
        50                  55                  60

<210> SEQ ID NO 50
```

```
<211> LENGTH: 60
<212> TYPE: PRT
<213> ORGANISM: Artificial Sequence
<220> FEATURE:
<223> OTHER INFORMATION: PpL mutant

<400> SEQUENCE: 50

Val Thr Ile Lys Glu Asn Ile Tyr Phe Glu Asp Gly Thr Val Gln Thr
1               5                   10                  15

Ala Gln Phe Lys Gly Thr Phe Ala Glu Ala Thr Ala Glu Ala Tyr Arg
            20                  25                  30

Tyr Ala Asp Leu Leu Ser Lys Glu His Gly Lys Tyr Thr Ala Asp Leu
        35                  40                  45

Glu Asp Gly Gly Tyr Thr Ile Asn Ile Arg Phe Ala
    50                  55                  60

<210> SEQ ID NO 51
<211> LENGTH: 302
<212> TYPE: PRT
<213> ORGANISM: Artificial Sequence
<220> FEATURE:
<223> OTHER INFORMATION: PpL mutant

<400> SEQUENCE: 51

Lys Glu Glu Thr Pro Glu Thr Pro Glu Thr Asp Ser Glu Glu Gln Val
1               5                   10                  15

Thr Ile Lys Glu Asn Ile Tyr Phe Glu Asp Gly Thr Val Gln His Ala
            20                  25                  30

Thr Phe Lys Gly Thr Phe Ala Glu Ala Thr Ala Glu Ala Tyr Arg Tyr
        35                  40                  45

Ala Asp Leu Leu Ser Lys Glu His Gly Lys Tyr Thr Ala Asp Leu Glu
    50                  55                  60

Asp Gly Gly Tyr Thr Ile Asn Ile Arg Phe Ala Gly Lys Glu Lys Thr
65                  70                  75                  80

Pro Glu Glu Pro Lys Glu Gln Val Thr Ile Lys Glu Asn Ile Tyr Phe
                85                  90                  95

Glu Asp Gly Thr Val Gln His Ala Thr Phe Lys Gly Thr Phe Ala Glu
            100                 105                 110

Ala Thr Ala Glu Ala Tyr Arg Tyr Ala Asp Leu Leu Ser Lys Glu His
        115                 120                 125

Gly Lys Tyr Thr Ala Asp Leu Glu Asp Gly Gly Tyr Thr Ile Asn Ile
    130                 135                 140

Arg Phe Ala Gly Lys Glu Lys Thr Pro Glu Glu Pro Lys Glu Gln Val
145                 150                 155                 160

Thr Ile Lys Glu Asn Ile Tyr Phe Glu Asp Gly Thr Val Gln His Ala
                165                 170                 175

Thr Phe Lys Gly Thr Phe Ala Glu Ala Thr Ala Glu Ala Tyr Arg Tyr
            180                 185                 190

Ala Asp Leu Leu Ser Lys Glu His Gly Lys Tyr Thr Ala Asp Leu Glu
        195                 200                 205

Asp Gly Gly Tyr Thr Ile Asn Ile Arg Phe Ala Gly Lys Glu Lys Thr
    210                 215                 220

Pro Glu Glu Pro Lys Glu Gln Val Thr Ile Lys Glu Asn Ile Tyr Phe
225                 230                 235                 240

Glu Asp Gly Thr Val Gln His Ala Thr Phe Lys Gly Thr Phe Ala Glu
                245                 250                 255

Ala Thr Ala Glu Ala Tyr Arg Tyr Ala Asp Leu Leu Ser Lys Glu His
```

```
            260                 265                 270
Gly Lys Tyr Thr Ala Asp Leu Glu Asp Gly Gly Tyr Thr Ile Asn Ile
                275                 280                 285

Arg Phe Ala Gly Lys Lys Val Asp Glu Lys Pro Glu Glu Cys
            290                 295                 300
```

<210> SEQ ID NO 52
<211> LENGTH: 906
<212> TYPE: DNA
<213> ORGANISM: Artificial Sequence
<220> FEATURE:
<223> OTHER INFORMATION: DNA code

<400> SEQUENCE: 52

```
aaagaagaaa ccccggaaac acctgaaact gattccgaag aacaagtaac cattaaagag    60
aacatctact tcgaagatgg cacagtacag catgccacgt ttaagggaac ctttgctgag   120
gctaccgccg aggcataccg ttatgcggac ttactgtcta aggaacacgg aaagtacacc   180
gctgacttag aagatggagg gtatactatc aatattcgct tcgccggtaa agaaaaaact   240
ccggaagaac ccaaagaaca ggtgactatc aaggaaaaca tttatttga ggacggcacc   300
gtgcaacatg cgacgtttaa aggcaccttc gccgaagcaa ccgcagaagc atatcgctat   360
gcggatctgc tcagtaagga acatgggaaa tataccgccg atctggaaga cggtggctac   420
acaattaaca tacgatttgc gggtaaggaa aaaccccag aggagccaaa agagcaggtt   480
accattaagg agaatattta tttcgaggat gggaccgtcc agcatgctac gttcaaaggt   540
acgtttgcgg aggcgacggc agaggcctat cgctacgccg atctactgag caaagaacac   600
ggtaaataca ctgcggacct tgaggatggc ggttacacga ttaacattcg tttcgcgggc   660
aaagagaaaa cgcccgaaga accgaaggaa caagtcacta tcaaagaaaa tatctacttt   720
gaagacggaa cggttcagca cgctaccttc aagggtacct ttgcagaagc cacagcggaa   780
gcctatcggt atgcagacct gctgtcgaaa gagcatggca atacacggc ggatttggaa   840
gatggggct ataccatcaa tatccgtttt gctggtaaaa aagtggatga aaaccggaa   900
gaatgc                                                              906
```

<210> SEQ ID NO 53
<211> LENGTH: 923
<212> TYPE: DNA
<213> ORGANISM: Artificial Sequence
<220> FEATURE:
<223> OTHER INFORMATION: DNA code

<400> SEQUENCE: 53

```
ctgcaggaaa agaagaaacc ccggaaacac tgaaactga ttccgaagaa caagtaacca    60
ttaaagagaa catctacttc gaagatggca cagtacagca tgccacgttt aagggaacct   120
ttgctgaggc taccgccgag gcataccgtt atgcggactt actgtctaag gaacacggaa   180
agtacaccgc tgacttagaa gatggagggt atactatcaa tattcgcttc gccggtaaag   240
aaaaaactcc ggaagaaccc aaagaacagg tgactatcaa ggaaaacatt tatttgagg   300
acggcaccgt gcaacatgcg acgtttaaag gcaccttcgc cgaagcaacc gcagaagcat   360
atcgctatgc ggatctgctc agtaaggaac atgggaaata taccgccgat ctggaagacg   420
gtggctacac aattaacata cgatttgcgg gtaaggaaaa accccagag gagccaaaag   480
agcaggttac cattaaggag aatatttatt tcgaggatgg gaccgtccag catgctacgt   540
tcaaaggtac gtttgcggag gcgacggcag aggcctatcg ctacgccgat ctactgagca   600
```

```
aagaacacgg taaatacact gcggaccttg aggatggcgg ttacacgatt aacattcgtt    660
tcgcgggcaa agagaaaacg cccgaagaac cgaaggaaca agtcactatc aaagaaaata    720
tctactttga agacggaacg gttcagcacg ctaccttcaa gggtaccttt gcagaagcca    780
cagcggaagc ctatcggtat gcagacctgc tgtcgaaaga gcatggcaaa tacacggcgg    840
atttggaaga tgggggctat accatcaata tccgttttgc tggtaaaaaa gtggatgaga    900
aaccggaaga atgctaatct aga                                            923

<210> SEQ ID NO 54
<211> LENGTH: 66
<212> TYPE: DNA
<213> ORGANISM: Artificial Sequence
<220> FEATURE:
<223> OTHER INFORMATION: oligo DNA

<400> SEQUENCE: 54
cgtggatccg aagaggttac cattaaagcg aacctgatct ttgccaatgg ctcgacacag     60
actgcc                                                                66

<210> SEQ ID NO 55
<211> LENGTH: 54
<212> TYPE: DNA
<213> ORGANISM: Artificial Sequence
<220> FEATURE:
<223> OTHER INFORMATION: oligo DNA

<400> SEQUENCE: 55
ggcgtaagct tctgaagtag ctttctcaaa cgtacctttg aactcggcag tctg            54

<210> SEQ ID NO 56
<211> LENGTH: 63
<212> TYPE: DNA
<213> ORGANISM: Artificial Sequence
<220> FEATURE:
<223> OTHER INFORMATION: oligo DNA

<400> SEQUENCE: 56
tcagaagctt acgcctatgc ggacacactc aagaaagaca atggcgaata cacagtggat     60
gtt                                                                   63

<210> SEQ ID NO 57
<211> LENGTH: 60
<212> TYPE: DNA
<213> ORGANISM: Artificial Sequence
<220> FEATURE:
<223> OTHER INFORMATION: oligo DNA

<400> SEQUENCE: 57
gatgaattct tagccggcga atttaatatt cagtgtgtaa cctttatctg caacatccac     60

<210> SEQ ID NO 58
<211> LENGTH: 66
<212> TYPE: DNA
<213> ORGANISM: Artificial Sequence
<220> FEATURE:
<223> OTHER INFORMATION: oligo DNA

<400> SEQUENCE: 58
cgtggatccg aagaggttac cattaaagtg aacctgatct ttgccgatgg caagactcag     60
actgcc                                                                66
```

<210> SEQ ID NO 59
<211> LENGTH: 54
<212> TYPE: DNA
<213> ORGANISM: Artificial Sequence
<220> FEATURE:
<223> OTHER INFORMATION: oligo DNA

<400> SEQUENCE: 59
gcggtaagct tctgcagtag cttcctcaaa cgtacctttg aactcggcag tctg    54

<210> SEQ ID NO 60
<211> LENGTH: 63
<212> TYPE: DNA
<213> ORGANISM: Artificial Sequence
<220> FEATURE:
<223> OTHER INFORMATION: oligo DNA

<400> SEQUENCE: 60
gcagaagctt accgctatgc ggacctgctc gcgaaagtca atggcgaata cacagcggat    60
ctg    63

<210> SEQ ID NO 61
<211> LENGTH: 63
<212> TYPE: DNA
<213> ORGANISM: Artificial Sequence
<220> FEATURE:
<223> OTHER INFORMATION: oligo DNA

<400> SEQUENCE: 61
gatgaattct tacttgccgg cgaatttaat attgattgtg taacctccat cttccagatc    60
cgc    63

<210> SEQ ID NO 62
<211> LENGTH: 201
<212> TYPE: DNA
<213> ORGANISM: Artificial Sequence
<220> FEATURE:
<223> OTHER INFORMATION: DNA code

<400> SEQUENCE: 62
gaagaggtta ccattaaagc gaacctgatc tttgccaatg gctcgacaca gactgccgag    60
ttcaaaggta cgtttgagaa agctacttca gaagcttacg cctatgcgga cacactcaag    120
aaagacaatg gcgaatacac agtggatgtt gcagataaag gttacacact gaatattaaa    180
ttcgccggct aagaattcat c    201

<210> SEQ ID NO 63
<211> LENGTH: 204
<212> TYPE: DNA
<213> ORGANISM: Artificial Sequence
<220> FEATURE:
<223> OTHER INFORMATION: DNA code

<400> SEQUENCE: 63
gaagaggtta ccattaaagt gaacctgatc tttgccgatg gcaagacaca gactgccgag    60
ttcaaaggta cgtttgagga agctactgca gaagcttacc gctatgcgga cctgctcgcg    120
aaagtcaatg gcgaatacac agcggatctg gaagatggag gttacacaat caatattaaa    180
ttcgccggca gtaagaatt catc    204

<210> SEQ ID NO 64
<211> LENGTH: 57

```
<212> TYPE: DNA
<213> ORGANISM: Artificial Sequence
<220> FEATURE:
<223> OTHER INFORMATION: oligo DNA

<400> SEQUENCE: 64
ggtaagcttc tgcagtagct tccgcaaacg tacctttgaa cgtggcaatc tgtaccg        57

<210> SEQ ID NO 65
<211> LENGTH: 57
<212> TYPE: DNA
<213> ORGANISM: Artificial Sequence
<220> FEATURE:
<223> OTHER INFORMATION: oligo DNA

<400> SEQUENCE: 65
ggtaagcttc tgcagtagct tccgcaaacg tacctttgaa cgtggccagc tgtaccg        57

<210> SEQ ID NO 66
<211> LENGTH: 57
<212> TYPE: DNA
<213> ORGANISM: Artificial Sequence
<220> FEATURE:
<223> OTHER INFORMATION: oligo DNA

<400> SEQUENCE: 66
ggtaagcttc tgcagtagct tccgcaaacg tacctttgaa cgtggcaccc tgtaccg        57

<210> SEQ ID NO 67
<211> LENGTH: 54
<212> TYPE: DNA
<213> ORGANISM: Artificial Sequence
<220> FEATURE:
<223> OTHER INFORMATION: oligo DNA

<400> SEQUENCE: 67
ggcgtaagct tctgaagtag ctttctcaaa cgtacctttg aaatcggcag tctg        54

<210> SEQ ID NO 68
<211> LENGTH: 54
<212> TYPE: DNA
<213> ORGANISM: Artificial Sequence
<220> FEATURE:
<223> OTHER INFORMATION: oligo DNA

<400> SEQUENCE: 68
gcggtaagct tctgcagtag cttcctcaaa cgtacctttg aactcggcat cctg        54

<210> SEQ ID NO 69
<211> LENGTH: 54
<212> TYPE: DNA
<213> ORGANISM: Artificial Sequence
<220> FEATURE:
<223> OTHER INFORMATION: oligo DNA

<400> SEQUENCE: 69
gcggtaagct tctgcagtag cttcctcaaa cgtacctttg aaatgggcag tctg        54

<210> SEQ ID NO 70
<211> LENGTH: 192
<212> TYPE: DNA
<213> ORGANISM: Artificial Sequence
<220> FEATURE:
<223> OTHER INFORMATION: DNA code

<400> SEQUENCE: 70
```

```
gaacaggtta ccattaaaga gaacatctac tttgaagatg gcacggtaca gattgccacg    60
ttcaaaggta cgtttgcgga agctactgca gaagcttacc gctatgcgga cctgctctcg   120
aaagagcatg gcaaatacac agcggatctt gaagatggag gttacacaat caatattcgc   180
ttcgccggct aa                                                        192

<210> SEQ ID NO 71
<211> LENGTH: 192
<212> TYPE: DNA
<213> ORGANISM: Artificial Sequence
<220> FEATURE:
<223> OTHER INFORMATION: DNA code

<400> SEQUENCE: 71
gaacaggtta ccattaaaga gaacatctac tttgaagatg gcacggtaca gctggccacg    60
ttcaaaggta cgtttgcgga agctactgca gaagcttacc gctatgcgga cctgctctcg   120
aaagagcatg gcaaatacac agcggatctt gaagatggag gttacacaat caatattcgc   180
ttcgccggct aa                                                        192

<210> SEQ ID NO 72
<211> LENGTH: 192
<212> TYPE: DNA
<213> ORGANISM: Artificial Sequence
<220> FEATURE:
<223> OTHER INFORMATION: DNA code

<400> SEQUENCE: 72
gaacaggtta ccattaaaga gaacatctac tttgaagatg gcacggtaca gggtgccacg    60
ttcaaaggta cgtttgcgga agctactgca gaagcttacc gctatgcgga cctgctctcg   120
aaagagcatg gcaaatacac agcggatctt gaagatggag gttacacaat caatattcgc   180
ttcgccggct aa                                                        192

<210> SEQ ID NO 73
<211> LENGTH: 192
<212> TYPE: DNA
<213> ORGANISM: Artificial Sequence
<220> FEATURE:
<223> OTHER INFORMATION: DNA code

<400> SEQUENCE: 73
gaagaggtta ccattaaagc gaacctgatc tttgccaatg gctcgacaca gactgccgat    60
ttcaaaggta cgtttgagaa agctacttca gaagcttacg cctatgcgga cacactcaag   120
aaagacaatg gcgaatacac agtggatgtt gcagataaag gttacacact gaatattaaa   180
ttcgccggct aa                                                        192

<210> SEQ ID NO 74
<211> LENGTH: 195
<212> TYPE: DNA
<213> ORGANISM: Artificial Sequence
<220> FEATURE:
<223> OTHER INFORMATION: DNA code

<400> SEQUENCE: 74
gaagaggtta ccattaaagt gaacctgatc tttgccgatg gcaagacaca ggatgccgag    60
ttcaaaggta cgtttgagga agctactgca gaagcttacc gctatgcgga cctgctcgcg   120
aaagtcaatg gcgaatacac agcggatctg gaagatggag gttacacaat caatattaaa   180
ttcgccggca agtaa                                                     195
```

<210> SEQ ID NO 75
<211> LENGTH: 195
<212> TYPE: DNA
<213> ORGANISM: Artificial Sequence
<220> FEATURE:
<223> OTHER INFORMATION: DNA code

<400> SEQUENCE: 75

```
gaagaggtta ccattaaagt gaacctgatc tttgccgatg gcaagacaca gactgcccat      60
ttcaaaggta cgtttgagga agctactgca gaagcttacc gctatgcgga cctgctcgcg     120
aaagtcaatg gcgaatacac agcggatctg gaagatggag gttacacaat caatattaaa     180
ttcgccggca agtaa                                                      195
```

<210> SEQ ID NO 76
<211> LENGTH: 60
<212> TYPE: PRT
<213> ORGANISM: Artificial Sequence
<220> FEATURE:
<223> OTHER INFORMATION: PpL mutant

<400> SEQUENCE: 76

```
Val Thr Ile Lys Glu Asn Ile Tyr Phe Glu Asp Gly Thr Val Gln Ile
1               5                   10                  15

Ala Thr Phe Lys Gly Thr Phe Ala Glu Ala Thr Ala Glu Ala Tyr Arg
            20                  25                  30

Tyr Ala Asp Leu Leu Ser Lys Glu His Gly Lys Tyr Thr Ala Asp Leu
        35                  40                  45

Glu Asp Gly Gly Tyr Thr Ile Asn Ile Arg Phe Ala
    50                  55                  60
```

<210> SEQ ID NO 77
<211> LENGTH: 60
<212> TYPE: PRT
<213> ORGANISM: Artificial Sequence
<220> FEATURE:
<223> OTHER INFORMATION: PpL mutant

<400> SEQUENCE: 77

```
Val Thr Ile Lys Glu Asn Ile Tyr Phe Glu Asp Gly Thr Val Gln Leu
1               5                   10                  15

Ala Thr Phe Lys Gly Thr Phe Ala Glu Ala Thr Ala Glu Ala Tyr Arg
            20                  25                  30

Tyr Ala Asp Leu Leu Ser Lys Glu His Gly Lys Tyr Thr Ala Asp Leu
        35                  40                  45

Glu Asp Gly Gly Tyr Thr Ile Asn Ile Arg Phe Ala
    50                  55                  60
```

<210> SEQ ID NO 78
<211> LENGTH: 60
<212> TYPE: PRT
<213> ORGANISM: Artificial Sequence
<220> FEATURE:
<223> OTHER INFORMATION: PpL mutant

<400> SEQUENCE: 78

```
Val Thr Ile Lys Glu Asn Ile Tyr Phe Glu Asp Gly Thr Val Gln Gly
1               5                   10                  15

Ala Thr Phe Lys Gly Thr Phe Ala Glu Ala Thr Ala Glu Ala Tyr Arg
            20                  25                  30
```

```
<210> SEQ ID NO 79
<211> LENGTH: 60
<212> TYPE: PRT
<213> ORGANISM: Artificial Sequence
<220> FEATURE:
<223> OTHER INFORMATION: PpL mutant

<400> SEQUENCE: 79

Val Thr Ile Lys Ala Asn Leu Ile Phe Ala Asn Gly Ser Thr Gln Thr
 1               5                  10                  15

Ala Asp Phe Lys Gly Thr Phe Glu Lys Ala Thr Ser Glu Ala Tyr Ala
            20                  25                  30

Tyr Ala Asp Thr Leu Lys Lys Asp Asn Gly Glu Tyr Thr Val Asp Val
        35                  40                  45

Ala Asp Lys Gly Tyr Thr Leu Asn Ile Lys Phe Ala
    50                  55                  60

<210> SEQ ID NO 80
<211> LENGTH: 60
<212> TYPE: PRT
<213> ORGANISM: Artificial Sequence
<220> FEATURE:
<223> OTHER INFORMATION: PpL mutant

<400> SEQUENCE: 80

Val Thr Ile Lys Val Asn Leu Ile Phe Ala Asp Gly Lys Thr Gln Asp
 1               5                  10                  15

Ala Glu Phe Lys Gly Thr Phe Glu Glu Ala Thr Ala Glu Ala Tyr Arg
            20                  25                  30

Tyr Ala Asp Leu Leu Ala Lys Val Asn Gly Glu Tyr Thr Ala Asp Leu
        35                  40                  45

Glu Asp Gly Gly Tyr Thr Ile Asn Ile Lys Phe Ala
    50                  55                  60

<210> SEQ ID NO 81
<211> LENGTH: 60
<212> TYPE: PRT
<213> ORGANISM: Artificial Sequence
<220> FEATURE:
<223> OTHER INFORMATION: PpL mutant

<400> SEQUENCE: 81

Val Thr Ile Lys Val Asn Leu Ile Phe Ala Asp Gly Lys Thr Gln Thr
 1               5                  10                  15

Ala His Phe Lys Gly Thr Phe Glu Glu Ala Thr Ala Glu Ala Tyr Arg
            20                  25                  30

Tyr Ala Asp Leu Leu Ala Lys Val Asn Gly Glu Tyr Thr Ala Asp Leu
        35                  40                  45

Glu Asp Gly Gly Tyr Thr Ile Asn Ile Lys Phe Ala
    50                  55                  60
```